(12) United States Patent
Coote et al.

(10) Patent No.: US 9,823,170 B2
(45) Date of Patent: Nov. 21, 2017

(54) METHOD, SYSTEM AND APPARATUS FOR USE IN LOCATING SUBSURFACE ORE BODIES

(75) Inventors: Stephen Coote, Cottesloe (AU); John Watling, Jandakot (AU)

(73) Assignee: GLOBAL SCIENTIFIC SERVICES PTY LTD, Cottesloe, Western Australia (AU)

( * ) Notice: Subject to any disclaimer, the term of this patent is extended or adjusted under 35 U.S.C. 154(b) by 335 days.

(21) Appl. No.: 14/001,277

(22) PCT Filed: Feb. 24, 2012

(86) PCT No.: PCT/AU2012/000182
§ 371 (c)(1),
(2), (4) Date: Nov. 4, 2013

(87) PCT Pub. No.: WO2012/113032
PCT Pub. Date: Aug. 30, 2012

(65) Prior Publication Data
US 2014/0047932 A1  Feb. 20, 2014

(30) Foreign Application Priority Data
Feb. 25, 2011  (AU) ................................ 2011900683

(51) Int. Cl.
*G01V 9/00* (2006.01)
*G01N 1/08* (2006.01)

(52) U.S. Cl.
CPC ............. *G01N 1/08* (2013.01); *G01V 9/007* (2013.01)

(58) Field of Classification Search
CPC .......... G01N 1/2205; G01N 1/10; G01N 1/08; B01L 2300/0681; G01V 9/007
(Continued)

(56) References Cited

U.S. PATENT DOCUMENTS 3,736,421 A * 5/1973 Strange .............. G01N 21/3504
250/341.1
4,056,969 A  11/1977 Barringer
(Continued)

FOREIGN PATENT DOCUMENTS

CA       2305960      * 10/2001
CN    101819169 A      9/2010
(Continued)

OTHER PUBLICATIONS

Translation of jp-270003.*
(Continued)

*Primary Examiner* — Helen Kwok
*Assistant Examiner* — Nashmiya Fayyaz
(74) *Attorney, Agent, or Firm* — Carlson, Gaskey & Olds

(57) ABSTRACT

A method and system for locating subsurface ore bodies. Samples of near surface soil are collected over a predetermined geographical area. The samples are analysed to discover any chemical anomalies in the dust particles as a way of identifying possible subcropping mineralization. A tine (22) and collection tube (24) engage into subsurface soil and samples are drawn up the tube into a dust collection module (12). Sub 5 micron particles are captured on an electrostatically charged tape (40). Consecutive samples are indexed on the tape e.g. with a barcode. Collected dust samples are ablated by a laser ablation cell (72) and the ablated sample analysed by a mass spectrometer for presence of ions indicating presence of a resource body, such as a body of ore, minerals or hydrocarbons.

39 Claims, 19 Drawing Sheets

(58) Field of Classification Search
USPC .......................... 73/863.23, 864.44, 864.45
See application file for complete search history.

(56) References Cited

U.S. PATENT DOCUMENTS

| | | | |
|---|---|---|---|
| 4,067,693 A | | 1/1978 | Wimberley |
| 4,441,616 A | * | 4/1984 | Konig ........................ B07C 5/36 |
| | | | 209/44.1 |
| H188 H | * | 1/1987 | Thomson ............ G01N 15/0618 |
| | | | 378/44 |
| 7,255,016 B2 | * | 8/2007 | Burton ...................... E02D 1/04 |
| | | | 173/19 |
| 7,552,654 B2 | | 6/2009 | Burton |
| 7,600,439 B1 | * | 10/2009 | Patterson ............... G01N 1/405 |
| | | | 73/23.37 |
| 2005/0041774 A1 | * | 2/2005 | Saitoh ................ B01D 46/0002 |
| | | | 378/53 |
| 2009/0193880 A1 | * | 8/2009 | Halverson ................ G01N 1/18 |
| | | | 73/64.56 |
| 2013/0206440 A1 | * | 8/2013 | Ikuta .................. B23Q 11/0046 |
| | | | 173/198 |

FOREIGN PATENT DOCUMENTS

| | | | |
|---|---|---|---|
| GB | 1446760 | | 8/1976 |
| JP | 270003 A | * | 10/1996 |
| RU | 1060973 | * | 12/1983 |

OTHER PUBLICATIONS

Machine translation of SU1060973.*
International Search Report and Written Opinion of the International Searching Authority for International application No. PCT/AU2012/000182.

* cited by examiner

METHOD, SYSTEM AND APPARATUS FOR USE IN LOCATING SUBSURFACE ORE BODIES

FIELD OF THE INVENTION

The present invention relates to a method, system and apparatus for identifying indicators of the presence and/or location of subsurface ore bodies.

BACKGROUND TO THE INVENTION

Current methods of locating subsurface ore bodies involve collecting soil samples from a number of locations across a prospective site and sending those samples for laboratory analysis to identify the potential for sub-surface ore deposits. Aerial surveys of the selected geographical area may also be conducted to assist in identifying likely deposit sites.

Known ways of collecting soil samples are labour-intensive and time-consuming, with significant potential for human error in the correct identification and accurate locating of soil samples across a site, as well as a risk of contamination of the samples. Transportation of soil samples to a laboratory is likewise expensive and fraught with the same potential for human error, as well as the protracted time in getting the samples from the site to a laboratory for analysis, analyzing each sample using a variety of instrumental techniques and more traditional techniques such as fire assay and then returning the results. Typically a period of several days or even weeks is needed to complete the analysis of all of the samples and return the results. Most analytical techniques involve the use of either mineral acid extractions, or fusion followed by spectrometric analysis. Fire assay procedures involve fusion for the sample with collection for gold and certain precious metals in a lead button, this button is then cupelled and either parted to remove silver and weighed or dissolved in mineral acid and subjected to spectrometric or spectrophotometric analysis for quantitation of the recovered precious metals. In more recent years, partial chemical leaches have also increasingly been used. These are based around the removal of a labile "coating" or a specific type of adsorbed chemical compound from a bulk soil matrix and in this way isolating the recently emplaced hydromorphic anomaly which, at the surface indicates the presence of deep or blind mineralization at depth. However, identification of hydromorphic anomalies is extremely difficult due to the extremely low concentration of hydromorphically-imposed ions compared to background levels of elements present in "background" soils or sediments. It has thus been found desirable to provide a method, system and apparatus to improve identification of, or to determine presence of, elements or compounds of interest in soil samples by detection of hydromorphic anomalies. The ability to determine the presence of hydromorphically emplaced anomalies above buried or blind ore bodies and in areas that are geochemically sterile as a result for thick and/or high iron content overburden opens up enormous areas of the world where exploration has heretofore been impractical, with particular reference to southern hemisphere countries such as Australia, South Africa, India and South American countries, for geochemical exploration. In addition, the fast and effective delineation of buried mineralization opens up the next generation of geochemical exploration through the possibility of determining the presence of mineralization that is not amenable to discovery through more traditional means of both geochemical and geophysical exploration.

One known system is disclosed in U.S. Pat. No. 4,056,969 to Barringer Research Limited. That document discloses a method and apparatus for geochemical exploration for mineral deposits in which particles contained on the surface of the earth are collected and analysed. A surface dust traverse is carried out whereby a land based vehicle, such as a truck, or aerial vehicle, such as a helicopter, trails a tube behind it over an area of land to be surveyed for presence of mineral deposits. Dust from the top millimeter of surface soil is collected by suction up the tube for analysis approximately every 105 meters. The background section of U.S. Pat. No. 4,056,969 discusses previous practices of sampling soil from 10 centimeters to 1 meter below the surface and the top 1 cm to 2 cms of soil are discarded to avoid contamination from animals or deposition of wind swept matter into the sampling area. U.S. Pat. No. 4,056,969 focuses on taking rapid samples from the very surface (top 1 millimeter) in order to identify by analysis the presence of micro-organisms that may indicate the presence of hydrocarbon deposits, or sampling from the same 1 milimeter or from vegetation to identify the presence of particulate materials. Even on water the method and system of U.S. Pat. No. 4,056,969 is only sampling the very surface of the water for particulates and micro-organisms as indicators of the presence of minerals or hydrocarbon deposits. There are obvious problems with such a sampling regime. Wind blown particulates can contaminate an area, particularly if there are mineral sands or other ore bodies being worked or transported within the region. Likewise, animals, such as farmed animals (cattle, sheep, goats etc.) or numbers of wild animals (kangaroos, horses, camels) using the area prior to sampling can contaminate the area. This can lead to erroneous analysis results.

U.S. Pat. No. 4,056,969 also only proposes the sampling and analysis of relatively large particles. Particles are sucked up the tube; however, particles above 200 micron (μm) are sieved out by a mesh screen. A jet spaced 2-3 cm away from a sampling tape allows large relatively heavy particles from within the 200 micron sample to impact the tape to capture a sample. Smaller, lighter particles below 50 micron size do not make it across the 2-3 cm space and are blown away from the tape as rejected material. Consequently, the system and method of U.S. Pat. No. 4,056,969 is only sampling particle sizes of between 200 micron and 50 micro size from the at surface soil. Such particles can be wind blown surface particles from another area, or may be carried in or deposited by vehicle movements or animals traversing the land. Such particles would not form part of the original soil surface but would be sampled and analsyed as if they were. U.S. Pat. No. 4,056,969 does not teach or disclose distinguishing original soil particles from foreign soil particles, and does not sample below the very surface of the soil, which could lead to erroneous results.

The collection tape used in U.S. Pat. No. 4,056,969 relies on an adhesive and an additional plastic cover tape to hold and protect the collected samples on the tape. The cover tape is rolled up with the collection tape once samples are blown onto the collection tape. This requires two tapes that must be aligned and rolled up together. There is a risk of one tape not properly covering the other, or the tapes not rolling up together. Either way, collected samples are at risk of contamination or damage.

Furthermore, the tube trailed behind the vehicle can get caught up as it is drawn across the surface, particularly on uneven or rocky ground or where there is vegetation. This can endanger the vehicle, particularly if a helicopter is used.

The present invention was developed with the aforementioned in mind. It provides a more efficient system, apparatus and method for identifying indicators of the presence and/or location of subsurface ore bodies that is less susceptible to the problem of human error or delay found in known systems.

References to prior art in this specification are provided for illustrative purposes only and are not to be taken as an admission that such prior art is part of the common general knowledge in Australia or elsewhere.

SUMMARY OF THE INVENTION

According to an aspect of the present invention there is provided a method for locating subsurface ore bodies, the method comprising:

taking near surface soil samples over a predetermined geographical area; and analysing material collected in the samples to discover any superimposed hydromorphic anomalies on dust particles as a way of identifying the possible presence of subsurface ore bodies.

Typically the dust particles, taken with each sample are micron, or preferably submicron, in size and as such have an extremely large surface area to volume ratio.

Preferably the samples are collected from sub-surface, such as within several centimeters from the actual surface. Preferred collection depth is between 75 mm and 150 mm.

According to another aspect of the present invention there is provided a method for detecting subsurface ore bodies, the method comprising:

taking a dust sample at each waypoint from an array of waypoints across a geographical area and recording location coordinates of each waypoint;

storing the dust samples in a contamination-free environment for subsequent analysis of any hydromorphic anomalies imposed onto the dust samples as a way of identifying the likely mineralisation associated with subsurface ore bodies. The array of waypoints may be in a regular grid pattern or may be an irregular pattern. Past and present practice is to take samples from tens or hundreds of waypoints across an area of interest. The location of each waypoint may be determined by GPS coordinates.

One or more embodiments of the present invention proposes taking samples from thousands of waypoints across a similar sized area. Automation of sample collecting reduces the number of people involved in collecting samples and increases speed of sampling. Improved speed of sampling and analysis techniques reduces the delay between obtaining the samples and outputting results of the analysis.

The position of each waypoint may be identified by a unique geographic position identifier or by an identifier relative to at least one reference point, such as a position relative to one or more other waypoints and/or to a fixed reference or datum point.

According to a further aspect of the present invention there is provided a method of collecting dust samples from a predetermined geographical area for detecting subsurface ore bodies, the method comprising:

transporting a sample collection apparatus over the geographical area according to a predetermined array of waypoints;

sampling the surface overburden at each waypoint using a probe;

in sampling the surface overburden, drawing a sample of dust from the surface overburden into a dust collection apparatus;

storing the dust sample from each waypoint in the dust collection apparatus; and, recording a unique location identifier corresponding to the geographical coordinates of each waypoint;

indexing each sample to the unique location identifier for that sample;

and analysing components in the dust samples to generate a plan of the geographical area identifying the indicated location of subsurface ore bodies based on the presence or of the components from each sample.

If an area is found to be depleted in a particular metal then that metal has been leached from the area. Knowing this gives insight into looking for the place where the leached metals have been deposited. Depletion has been found to be very useful as a potential indicator of localized enrichment somewhere else. If a metal is absent over a large area, this may be an indication to look somewhere close for a depositional environment where the leached material has been dumped to form an actual ore body.

Analysis may look for hydromorphic anomalies of components within the sample(s) taken.

According to a yet further aspect of the present invention there is provided a method of generating a visual representation of the presence of subsurface ore bodies in a geographical area, the method comprising:

collecting dust samples from the geographical area;

simultaneously recording geographical coordinates of the location of each dust sample collected;

analyzing fine particles of dust from the dust samples to discover any superimposed hydromorphic anomalies in the dust particles as a way of identifying the possible presence of subsurface ore bodies;

processing the results of the analysis and combining the geographical coordinates of the dust particles with the results superimposing on a map of the geographical area the processed results A variety of colours may be used to generate a visual effect indicating the possible mineralisation of subsurface ore bodies.

The visual effect may take the form of plots or maps in two or three dimensions. The geographical coordinates or location may be defined by global positioning system (GPS) coordinates.

According to another aspect of the present invention there is provided a method of collecting, locating and storing and subsequently identifying dust samples and relating analytical data back to a specific dust sample from a geographical area for detecting subsurface ore bodies, the method comprising:

storing particles of dust onto a substrate from a dust sample collected from at least one waypoint on the geographical area;

transporting the substrate in a controlled environment from a substrate feed device to a substrate receiver;

obtaining the geographical location of each dust sample across the geographical area from which the dust particles have been collected;

reading a unique identifying code for each dust sample from the filter tape; and, storing the geographical location together with the unique identifying code for each dust sample whereby, in use, subsequent analysis for any components of interest within the dust samples are used to identify the potential presence of subsurface ore bodies.

The components within the dust may be hydromorphic components indicating the potential mineralization of subsurface ore bodies.

The substrate may include or form a filter medium, and may be in the form of a tape. The substrate may be a continuous strip of a material incorporating a filter medium. For example, the substrate may be a tape wound onto opposed reels or spools such that the tape travels from one reel/spool to the other when the system and method are implemented.

The controlled environment may include a contamination free environment, temperature controlled or humidity controlled environment, or one or more thereof.

The substrate feed device may include a first reel or spool, and the substrate receiver may include a second reel or spool. As above, the substrate may therefore act as a tape medium fed between the first and second reels/spools.

The geographical location may be determined from GPS coordinates or other reference(s) as mentioned above.

According to a still further aspect of the present invention there is provided a system for collecting dust samples from a geographical area for locating subsurface ore bodies, the system comprising:

a dust collection module for storing dust samples in a controlled environment;

means for transporting the dust collection module over terrain in the geographical area;

a sampling probe connected to the dust collection module and arranged to be inserted into the surface overburden at selected locations; and, a sampler associated with the sampling probe to, in use, draw a sample of dust up into the dust collection module from each selected location; and indexing means matching each sample with the corresponding location from within the geographical area.

The dust samples are captured for subsequent analysis. Such analysis may look for the presence, concentration and/or variety of hydromorphic components in the dust samples in order to identify potential mineralization.

A yet further aspect of the present invention provides a dust collection module for collecting dust samples from a geographical area for locating subsurface ore bodies, the module comprising:

a dust sample storage container for storing dust samples in a controlled environment;

a transport mechanism arranged to index a substrate of dust sample retaining material housed within the container;

means for drawing dust particles from a dust sample onto the substrate, each dust sample indexed to a sequential position on the substrate; and, means for reading a unique identifier on the substrate identifying each dust sample at the indexed position, such that each dust sample can be identified with its geographical location and subsequently analyzed for indicators within the dust sample that may suggest the presence or mineralisation of subsurface ore bodies.

The dust sample retaining material may be a filter paper or a web of material supporting a filter paper.

The indicators may be chemical elements.

According to another aspect of the present invention there is provided a sampling probe for collecting dust samples from a geographical area for locating subsurface ore bodies, the probe comprising:

a tine adapted to penetrate surface overburden soil;

a dust collection tube provided in connection with the tine for transporting dust samples from the tip of the tine to a dust collection module whereby, in use, the dust samples can be subsequently analyzed for any hydromorphic components that may indicate the mineralisation of subsurface ore bodies.

Preferably the sampling probe further comprises a depth-control mechanism for controlling the depth to which the tine penetrates the soil. Preferably the tine penetrates to a depth of between 50 mm to 150 mm; more typically about 80 mm to 120 mm.

According to another aspect of the present invention there is provided a method of analysing dust samples from a geographical area for locating subsurface ore bodies, the method comprising:

ablating particles of dust from a dust sample;

analysing the chemical composition of the ablated dust particles for the presence of elemental anomalies associated with mineralization; and using the analysis to determine the potential presence of subsurface ore bodies.

Analysis may be carried out by either or both spectrometric and spectroscopic techniques. The use of Inductively Coupled Plasma Mass Spectrometric (ICP-MS) techniques is preferred. This s technique can detect presence of elements at levels down to parts per trillion for a wide range of elements (i.e. 60+elements) almost simultaneously.

According to a further aspect of the present invention there is provided a method of processing dust samples collected from a geographical area for detecting subsurface ore bodies, the method comprising:

providing an indexed filter medium having particles of dust deposited thereon from each dust sample collected transporting the filter medium in a contamination-free environment through a laser ablation cell;

ablating particles of dust from each dust sample;

providing a unique identifying code for each dust sample from the filter tape;

performing geochemical analysis of the ablated materials to determine the potential presence of any elemental anomalies; and, digitally recording the results of the geochemical analysis, the unique identifying code, and the GPS coordinates of the location for each sample from which the dust particles have been obtained whereby, in use, the recorded data can be used to identify the mineralization presence of subsurface ore bodies.

The elemental anomalies may be hydromorphic anomalies, such as ions of particular elements or compounds attached to dust particles.

The indexed filter medium may be coded at each index point such that each index point is uniquely identifiable from another index point. Coding may be by way of a unique serial number, barcode or other readable unique indicator.

The filter medium may be a filter paper tape, such as provided between two reels or spools. However, the filter medium may have a backing substrate with a continuous or discontinuous filter medium applied thereto. The backing substrate may have apertures corresponding to indexed positions for the respective samples such that a dust sample is applied to the filter medium over an aperture in the substrate. Thus, the filter medium may be a laminated material, such as a synthetic plastics or natural material based backing substrate and a paper based filter medium.

According to a yet further aspect of the present invention there is provided a method of processing data relating to dust samples collected from a geographical area for detecting subsurface ore bodies, the method comprising:

retrieving data relating to geochemical analysis, a unique identifying code, and GPS coordinates of the location of each dust sample; and, generating a map of the geographical area from which the dust samples were collected and superimposing on the map a graphical representation of the analytical data.

According to another aspect of the present invention there is provided a system for analysing dust samples from a geographical area for locating subsurface ore bodies, the system comprising:

an ablation means for ablating particles of dust from a dust sample and, analysis means for analysing the chemical composition of the ablated dust particles for the presence of hydromorphic anomalies that may indicate the mineralogy of subsurface ore bodies.

According to a further aspect of the present invention there is provided a system for analyzing dust samples collected from a geographical area for use in detecting subsurface ore bodies, the system comprising:

a sample reel with a coded filter tape having particles of dust deposited thereon from each dust sample collected;

a tape transport mechanism for receiving the sample reel and transporting the filter tape in a controlled environment to a take-up reel;

a laser ablation means provided in connection with the tape transport mechanism for ablating particles of dust from each dust sample as the tape passes there through; means for reading a unique identifying code for each dust sample from the filter tape.

The system may include analysis means for performing geochemical analysis of the ablated materials for elemental anomalies. The anomalies may be hydromorphic anomalies. Finding hydromorphic anomalies will indicate sub-cropping mineralization.

The analysis means (equipment) may be adjacent or near to the tape transport and laser ablation means or may be provided remotely. For example, analysis may be carried out in situ with sample collection and ablation or the samples may be removed to a remote location for analysis, such as at a laboratory. Removal to a remote location can allow the rest of the system to be used in the field (in situ) to collect further samples from the same site or the system can be removed to a fresh site, means for digitally recording the results of the geochemical analysis, the unique identifying code, and the GPS coordinates of the location for each dust sample from which the dust particles have been obtained whereby, in use, the recorded data can be used to identify the potential for subsurface mineralization.

The controlled environment may be a contamination-free environment, such as in a sealed container. The sealed container may be an openable hard case containing the transport mechanism, the reels and the laser ablation means.

With the aforementioned in view, one or more forms of the present invention provides a method for locating subsurface ore bodies, the method comprising:

taking dust samples of near surface soil over a predetermined geographical area; and analysing particles of dust from the dust samples to discover any hydromorphic anomalies in the dust particles as a way of identifying the possible mineralisation of subsurface ore bodies.

The method may include establishing a grid pattern of waypoints for taking the dust samples in a preselected geographical area; and taking a dust sample at each waypoint according to the grid pattern and simultaneously recording the GPS coordinates of each waypoint.

A preferred embodiment includes storing the dust samples in a contamination-free environment for conducting the analysis for hydromorphic anomalies in the dust samples.

The method may include transporting a dust collection apparatus over the terrain in the geographical area according to predetermined waypoints;

inserting a sampling probe into the surface soil at selected ones of said waypoints;

drawing a sample of dust up into the dust collection apparatus;

storing the dust sample from each waypoint in the dust collection apparatus in a contamination-free environment; and, recording the GPS coordinates of each selected waypoint whereby, in use, the analysis for any hydromorphic components in the dust samples is used to determine the potential mineralisation of subsurface ore bodies.

Preferably the present invention includes generating a visual representation of possible subsurface ore bodies in the geographical area based on results from the analysis.

Recording GPS coordinates of the location of each dust sample may be conducted substantially simultaneously with the collecting and storing of the dust samples.

Statistical manipulation of the results of the analysis may be conducted.

The method may include combining GPS coordinates of the dust particles with the results of the statistically manipulated data; and, superimposing on a map of the geographical area the results of the statistically manipulated data to generate a map indicating the possible location of subsurface ore bodies.

Statistical manipulation of data may include averaging data results.

Preferably one or more embodiments comprises storing the particles of dust from each dust sample collected at a respective waypoint onto an indexed filter medium.

The or each dust sample may be sucked onto, blown onto or otherwise delivered onto the filter medium.

The dust samples taken for analysis will preferably be fine grained and preferably in a size range below 1.0 micron but may be larger than 1.0 micron.

The method may include transporting a tape containing filter medium from a first reel onto a second reel in a contamination-free environment.

Preferably the method includes reading a unique identifying code for each dust sample from the filter tape; and storing GPS coordinates together with the unique identifying code for each dust sample whereby, in use, subsequent analysis for any hydromorphic components in the dust samples is used to identify mineralisation of subsurface ore bodies.

A system for collecting dust samples from a geographical area for locating subsurface ore bodies, the system comprising:

a dust collection module for storing dust samples in a controlled environment;

means for transporting the dust collection module over terrain in the geographical area;

a sampling probe mechanically coupled to the dust collection module;

an insertion means actuated in use to insert the probe into the terrain surface at selected locations; and, sample retrieving means provided in connection with the sampling probe for drawing a sample of dust up into the dust collection module whereby, in use, subsequent analysis for any hydromorphic components in the dust samples can be performed for identifying the potential mineralisation of subsurface ore bodies.

The dust collection module may comprise a container for storing dust samples in a contamination-free environment; and a transport mechanism for an indexed filter medium housed within the container.

Dust particle drawing means to draw fine particles of the dust onto the filter medium may be employed.

The system may further include a unique code provided for each dust sample indexed on the filter medium; and a code reader provided on the filter medium.

The sampling probe may comprise a tine adapted to penetrate surface overburden soil and a dust collection tube provided in connection with the tine for transporting dust samples from adjacent the tip of the tine to the dust collection module.

An ablation means may be provided arranged to ablate particles of dust from a collected dust sample. The ablation means may be housed in the dust collection module.

The collection module may house a sample reel with a coded filter tape having particles of dust deposited thereon from each dust sample collected, and a tape transport mechanism for receiving the sample reel and transporting the filter tape in a contamination-free environment to a take-up reel.

The system may include an analyzer for performing geochemical analysis of ablated dust particles for detecting hydromorphic anomalies.

Digital recording means to record results of the geochemical analysis may be provided as part of the system.

The system may include providing a unique identifying code and GPS coordinates of the location for each dust sample from which the dust particles have been obtained. To this end, a code imprinting means may be provided to mark the filter medium at or to create indexed positions.

Throughout the specification, unless the context requires otherwise, the word "comprise" or variations such as "comprises" or "comprising", will be understood to imply the inclusion of a stated integer or group of integers but not the exclusion of any other integer or group of integers.

Likewise the word "preferably" or variations such as "preferred", will be understood to imply that a stated integer or group of integers is desirable but not essential to the working of the invention.

BRIEF DESCRIPTION OF THE DRAWINGS

The nature of the invention will be better understood from the following detailed description of a specific embodiment of the method and system for locating subsurface ore bodies, given by way of example only, with reference to the accompanying drawings, in which:

FIG. 15 shows the shuttle mechanism in a cleaning position, and FIG. 16 shows the shuttle mechanism in a sampling position.

DETAILED DESCRIPTION OF PREFERRED EMBODIMENTS

Figure 1:
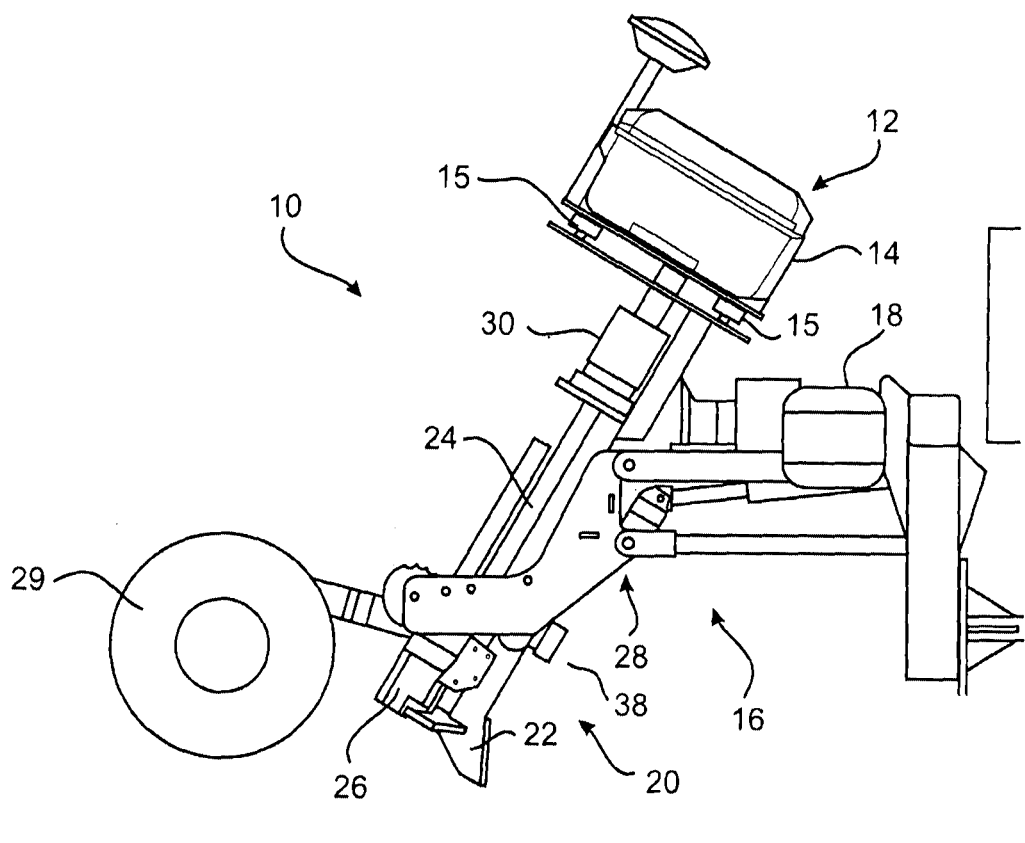
FIG. 1 shows a view of a system for collecting dust samples in accordance with a preferred embodiment of the present invention, the tine and collection tube in a raised position.

Embodiments of the present invention will hereinafter be described with reference to the accompanying drawings.

The present invention is based on the discovery that geochemical analysis of hydromorphically deposited ions on fine dust particles from near surface soil samples can be used to predict with some accuracy the mineralisation of subsurface ore bodies. Preferably the deposited ions are sampled within a depth of less than 1 meter from the soil surface, and more preferably within a depth of 20 cm from the surface.

The dust particles can be collected and stored in a controlled environment, such as a contamination-free environment. It has been realized that the presence of subsurface ore bodies can be identified to depths of up to 150 m or more.

The dust particles may be in the micron to sub-micron size, preferably less than 10 micron, and more preferably between about 0.1 to 4.0 micron in size.

Embodiments of the present invention collect sub 5 micron particle size ions from below the surface, that form around the sub 5 micron particle at depth, and are thereto transported to the surface via a hydromorphic effect. The smaller the particle the larger the mass of ions coating the particle surface, the greater the potential to show an anomalous find. The system and method disclosed in known U.S.

Pat. No. 4,056,969 discards these sub 5 micron particles, and does not sample below the surface.

It has been realized that sub 5 micron size particles have accumulated a greater density of ions than larger particles. Thus, a greater proportion of a given sample will have ions attached, thereby giving improved sampling results than the use of larger particles.

By collecting 'small' micron size dust particles, the much higher ratio of hydromorphic deposits of elements on such "small" particles compared to the larger particles and grains collected in conventional geochemistry, leads to stronger differentiation of each element from "background" and thus to improved acuity and depth of detection.

Because of the relatively small size of the dust particles, the hydromorphically deposited elements of each particle will comprise a far greater percentage of the entire mass of the particle. The ratio of the volume of hydromorphically deposited elements to the volume of the grain is much greater for each small grain of dust than it is to larger grains of dust and soil. It has been realized that the smaller the particle the greater percentage a specific thickness of imposed coating will be of the entire mass. The coating comes from liquids that are carried past and through any deeply buried mineralization and consequently the greater the percentage of the material that you are analyzing is from buried mineralization the clearer will be the indication of that mineralization in the analytical data. Therefore the hydromorphic component of the material will be proportionally larger leading to an increase in the likelihood of successfully discovering buried and blind subsurface ore bodies.

Buried ore bodies are ore bodies that are covered but have no material in that covering which will limit the movement of abraded material to the surface soil, blind ore bodies have coverings of rock that will prevent mechanical incorporation of ore material into the surficial soil.

An important feature of one or more embodiments of the present invention is the ability and means to collect dust samples efficiently in the field and to store and transport them in a contamination-free environment for subsequent analysis.

Figure 2:
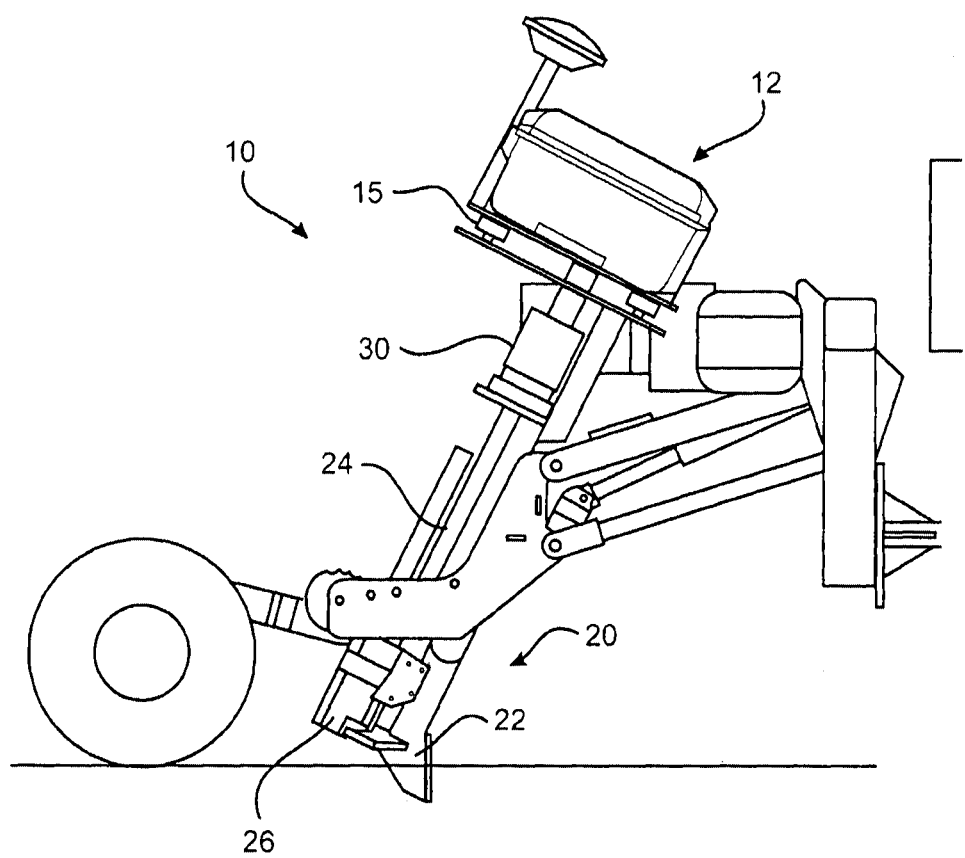
FIG. 2 shows a view of the system of FIG. 1 as it starts to penetrate the soil with the tine and collection tube in a partially lowered position.
Figure 3:
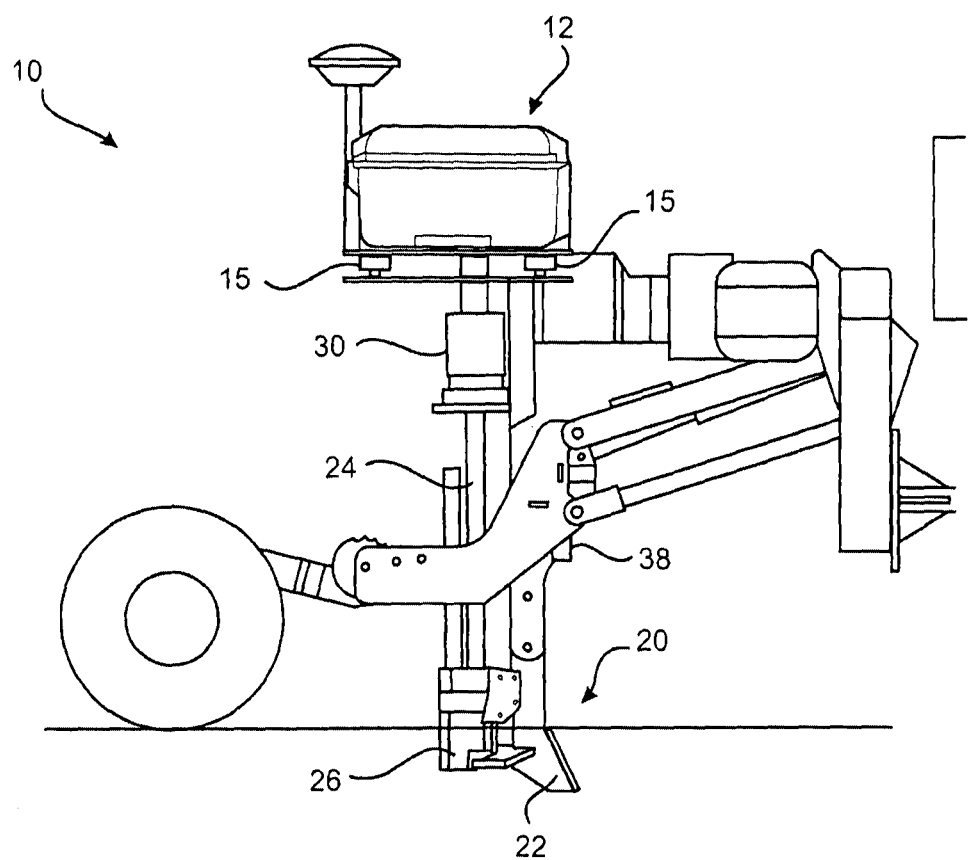
FIG. 3 shows a view of the system of FIG. 1 in an operational position with the tine engaging the ground ahead of the collection tube.

A preferred embodiment of a system for collecting dust samples from a geographical area for locating subsurface ore bodies in accordance with the invention, as illustrated in FIGS. 1 to 3, comprises a dust collection module 12 for storing dust samples in a contamination-free environment. The dust collection module 12 includes a casing 14 housing an apparatus for storing the dust samples, as will be described in more detail below with reference to FIGS. 5 to 8.

The system 10 for collecting dust samples also includes means for transporting the dust collection module 12 over the terrain in the geographical area. In the illustrated embodiment the transporting means comprises an adjustable support assembly 16 mounted on the rear of a motor vehicle (not shown) such as a 4WD or specialised all-terrain vehicle. The transporting means may be of any suitable form including an aerial vehicle such as, for example, as unmanned aerial vehicle (UAV). The transporting means may also take the form of a back-pack for transporting the system 10 by foot.

In the illustrated embodiment the adjustable support assembly 16 is hydraulically operated and is provided with its own power pack 18 for lowering and raising the system 10 to/from an operating position. In FIG. 1 the system 10 is shown in it raised position, where it is held during transport to the geographical area where dust samples are to be collected, and between waypoints in the geographical area when the dust samples are being collected.

A power take off (PTO) of the vehicle can be used to drive a compressor and/or hydraulic pump to supply compressed air and/or hydraulic pressure to lower/raise the tine. The system can therefore be self contained and powered on the vehicle without requiring an additional power supply. The compressed air can also be used to provide filtered, de-humidified air to clean the collection tube.

The system 10 for collecting dust samples further comprises a sampling probe 20, mechanically coupled to the dust collection module 12, and adapted to be momentarily inserted into the surface overburden at selected locations. The sampling probe 20 may be handheld device. In the illustrated embodiment the sampling probe 20 comprises a tine 22 adapted to penetrate surface overburden soil, and a dust collection tube 24 provided in connection with the tine 22 for transporting dust samples from adjacent the tip of the tine 22 to the dust collection module 12. It will be appreciated that the collection tube follows directly behind the tine. The tine acts to create a groove through the surface soil while the collection tube provides a conduit for a soil sample to be sucked up to the collection module. A collecting head 26 provided at a lowermost extremity of the dust collection tube 24 is located immediately behind the tip of the tine 22, and has a mouth (not visible) that faces in the opposite direction to the direction of travel of the tine 22, which assists in preventing blockage of the end of the collection tube.

Preferably the sampling probe 20 also comprises a depth-control mechanism 28 with hydraulic actuator for controlling the depth to which the tine 22 penetrates the soil. The depth-control mechanism 28 includes a jockey wheel 29. The height of the jockey wheel can be readily adjusted to set the penetration of the tine to the required depth. Such height adjustment may be by way of a rotary actuator with height position settings, such as notches indexing different height settings.

Preferably, in use, the tine penetrates to a depth of between 2 mm to 150 mm; more preferably between about 80 mm to 100 mm. A load cell 38, mounted in connection with tine 22, provides additional important information relating to soil compression for the geologists.

The load cell pressure is collated with each sample and represented as a measurement in Newton (N) (force). Measurements of ambient humidity and air temperature are also provided for the geologists to interpret.

The tine 22 is mounted on a break-away leg with an adjustable break-away pressure. The break-away leg is designed to allow the tine 22 to swing 20 upwards away from any obstacle it may encounter in the soil, such as a rock, so as to avoid damaging the collecting head 26. Typically the break-away pressure is set at about 250 kg, though the break-away pressure may be adjusted to suit types of overburden soil and rock content.

The system 10 further comprises means provided in connection with the sampling probe 20 for drawing a sample of dust up into the dust collection module 12 whereby, in use, subsequent analysis for any hydromorphic components in the dust samples can be performed for identifying the potential mineralisation of subsurface ore bodies. In this embodiment the means for drawing the dust samples comprises a vacuum pump 30 which is adapted to draw a sample dust stream into the mouth of the collecting head 26 and upwards through the dust collection tube 24 to the dust collection module 12. The dust collection module 12 comprises a casing 14 for storing dust samples in a contamination-free environment, as can be seen most clearly in FIGS. 5 to 8. The casing 14 is preferably a heavy-duty military back pack with removable lid that can be clamped shut to form an airtight enclosure. The casing 14 is preferably mounted on four Barry Mounts 15. The 'Barry Mounts' 15 are anti-vibration devices that employ an oil cushion to isolate the casing 14 from vibrations transported upwards from the sampling probe 20. A tape transport mechanism 32 is housed within the casing 14 for transporting a coded filter tape 40 from a sample reel 36 to a take-up reel 38. The coded filter tape 40 is made from a special porous material that captures dust particles greater than about 0.45 micron in diameter in the pores of the material. The filter tape 40 preferably has barcodes printed onto its surface at spaced intervals to permit each sample captured on the tape to be uniquely identified. The tape is preferably a composite polymer that, during manufacturing or post manufacturing, is subject to being rolled and rolled. This causes an electrostatic charge that attracts the sub 5 micron particles to stick to backing or webbing in the tape. The electrostatic charge remains when the particles are impinged onto the tape. Thus no adhesive is required, and no additional cover tape is required. The electrostatic charge on the tape readily retains the smaller (sub 5 micron) particles and does not hold many, if any, larger particles. Thus, the technological benefits of the tape having an electrostatic charge to hold particles provides benefits over adhesive tapes. Also, only requiring one layer of tape, rather than the adhesive tape and second roll of cover tape, of U.S. Pat. No. 4,056,969, allows rolls of tape to either be longer in length for a given thickness or take up less room in the ablation unit.

Tape spools or reels can be each be orientated vertically rather than horizontally within the tape housing's sealed container. In use, the tape is moved into position and sealed within the collection tube ready to receive the dust stream and take the sample. The tape and its reels/spools 9 preferably housed in a cartridge) are moved horizontally, approximately 100 mm, away from and sealed from the dust collection tube whilst the collection tube is blasted with high pressure dehumidified pre-filtered compressed air. This prevents damage to the tape and contamination during the high pressure cleaning process. At the same, time the control system advances the tape to the next sample ready for repositioning during cleaning. This speeds up the entire sample collection process because two processes are completed at the same time.

The tape transport mechanism 32 can include a tension step motor (not visible) for rotating the sample reel 36, and maintaining a predetermined tension on the filter tape 40, and a take-up step motor (not visible) for rotating the take-up reel 38 and for winding the tape 40 onto the take-up reel 38 in stepped increments. The step motors are typically brushless 12 volt DC motors which enable remote computer adjustable torque, tension and speed control. Drive to one or both of the reels within the casing may be provided externally of the casing, such as by one or more corresponding externally mounted motors. This can reduce the overall weight of the casing and complexity of the equipment therein. A tape pinch stepper 42 also helps to maintain the tension on the filter tape 40. The tape can be held and advanced rather than relying on rotation of reels/spools as an advancing mechanism. For example, the reels/spools may be freely rotating or have low rotational resistance, and the holding mechanism is sufficient to retain the tape and move it such the reels/spools rotate in synch with that movement. A combination of driven reel(s)/spool(s) and tape holding advancement may be employed.

A barcode reader 44 is also provided in the casing 14 for reading the unique barcodes printed on the filter tape 40 for identifying each dust sample. Although barcodes are preferably used, other unique sample identifiers can be used, such as unique alphanumeric codes or other optical machine readable codes.

The dust collection module 12 further comprises a means for drawing dust particles from a dust sample onto the filter tape 40. In this embodiment, a stream of dust particles from the dust sample is drawn upwards through the dust collecting tube 24 into an elbow-shaped tube 46 inside the casing 14. As can be seen more clearly in FIG. 7, the elbow-shaped tube 46 has a mass suction fan 48 provided within it at the point where the tube 46 exits the casing 14. The mass vacuum fan 48 draws the main stream of dust particles through the dust collection module 12. A small sample tube 50 extends into the interior 13 of the elbow-shaped tube 46 (see FIG. 7) for taking a sample of dust particles from the main dust stream. A sample vacuum fan 52 is provided for sucking the sample of dust particles through a small channel 54, which passes through the transport path of the filter tape 40, into an evacuation chamber 56.

The strength of the respective vacuums created by the fans 48 and 52 respectively is carefully calibrated to ensure that only fine dust particles within the preferred particle size range (0.1 to 10.0 micron, preferably up to 4.0 micron) are suspended in the air stream that passes through the filter tape 40. A significant number of these fine dust particles are deposited on the filter tape 40, in a designated area on the tape adjacent a barcode, for storage and subsequent analysis. The series of vacuum suction tubes thus provided eliminate dust particles with a size greater than 4 micron, using a four zone stepped vacuum system with adjustable vacuum controls in each zone.

After each sample of fine dust particles is collected, the entire four zone dust transport pathway has to be cleaned of residual dust particles to prevent contamination of the next dust sample. For this purpose an air nipple 58 is provided in fluid connection with the dust transport pathway. A source of compressed air is connected to the air nipple 58, and after each dust sample collection sequence, a blast of compressed air is sent through the dust transport pathway to evacuate it of any residual dust particles. As can be seen most clearly in FIG. 7, a pivotable cylindrical member 62 is provided in the dust transport pathway, adjacent to the point where the fine dust particles are directed onto the filter tape via the small sample tube 50. The cylindrical member 62 has a T-shaped channel provided through it for redirecting the flow path from the filter tape to the air nipple 58. The cylindrical member 62 is pivoted after each sample is collected, so that a blast of compressed air is sent back through the dust transport pathway in the opposite direction to that in which it flowed when collecting the sample. Any residual dust particles are thus evacuated back out through the dust collection tube 24.

Figure 4:
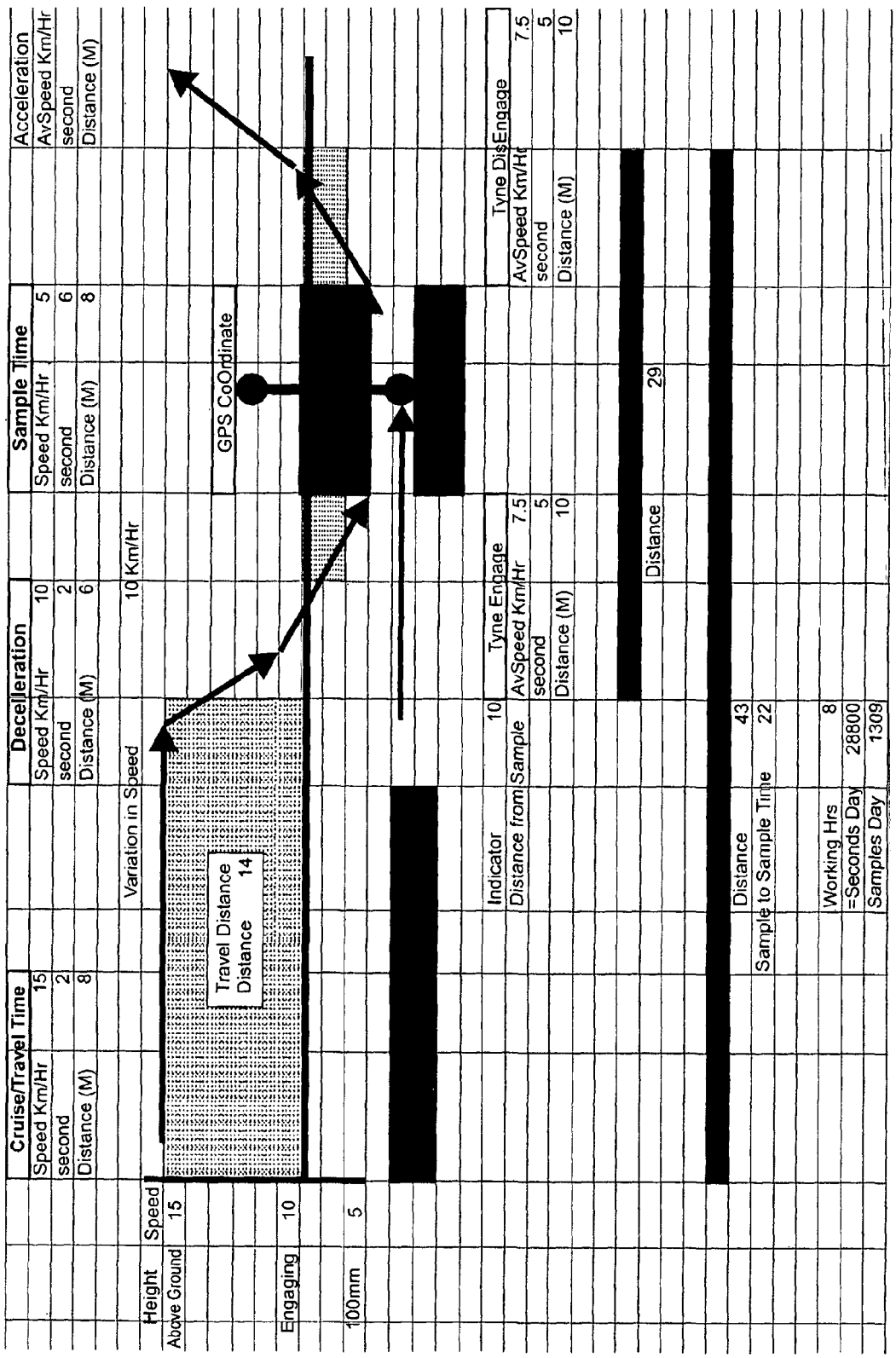
FIG. 4 illustrates in a graphical format a method of collecting dust samples in accordance with a preferred embodiment of the present invention.
Figure 5:
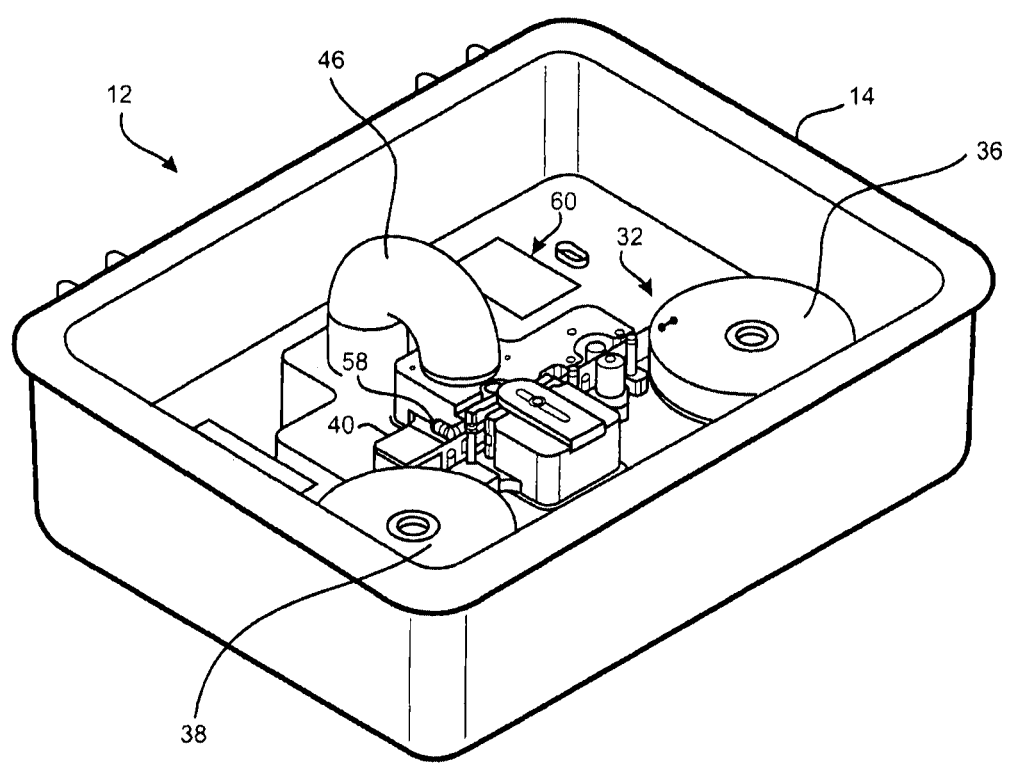
FIG. 5 is a top perspective view of a dust collection module employed in the system of FIG. 1.
Figure 6:
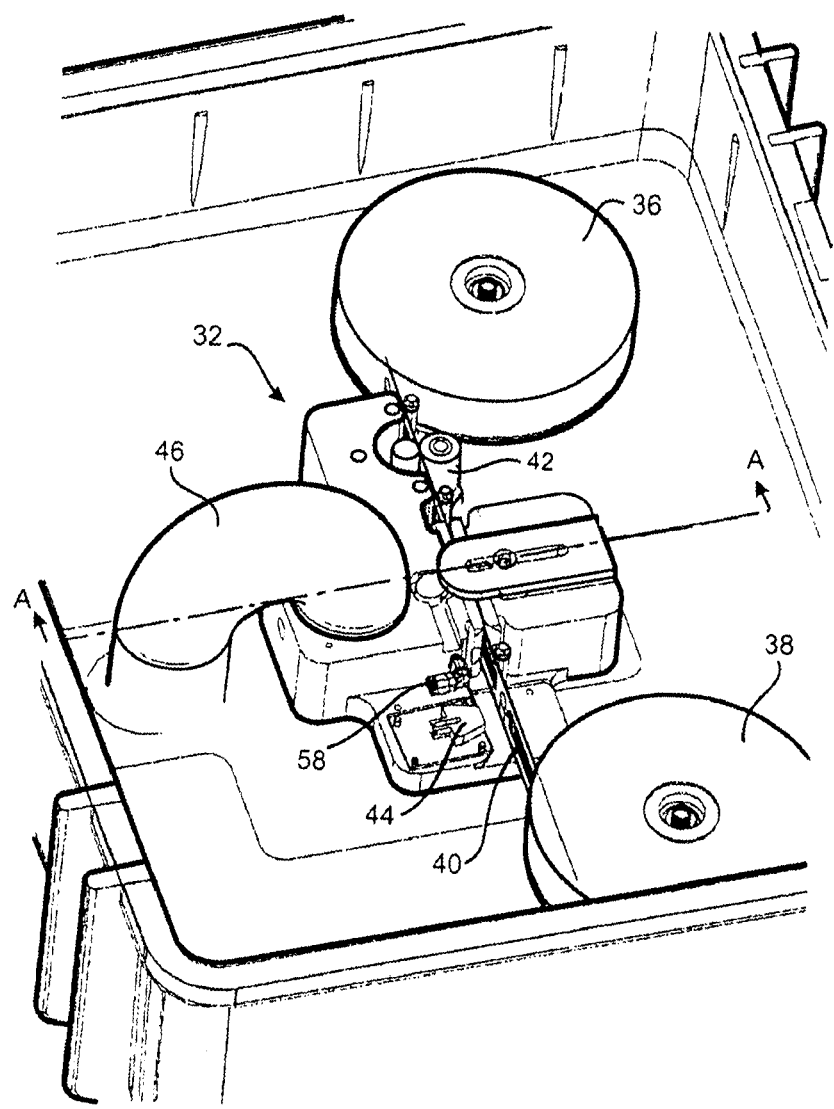
FIG. 6 is an enlarged top perspective view of the dust collection module of FIG. 5.
Figure 7:
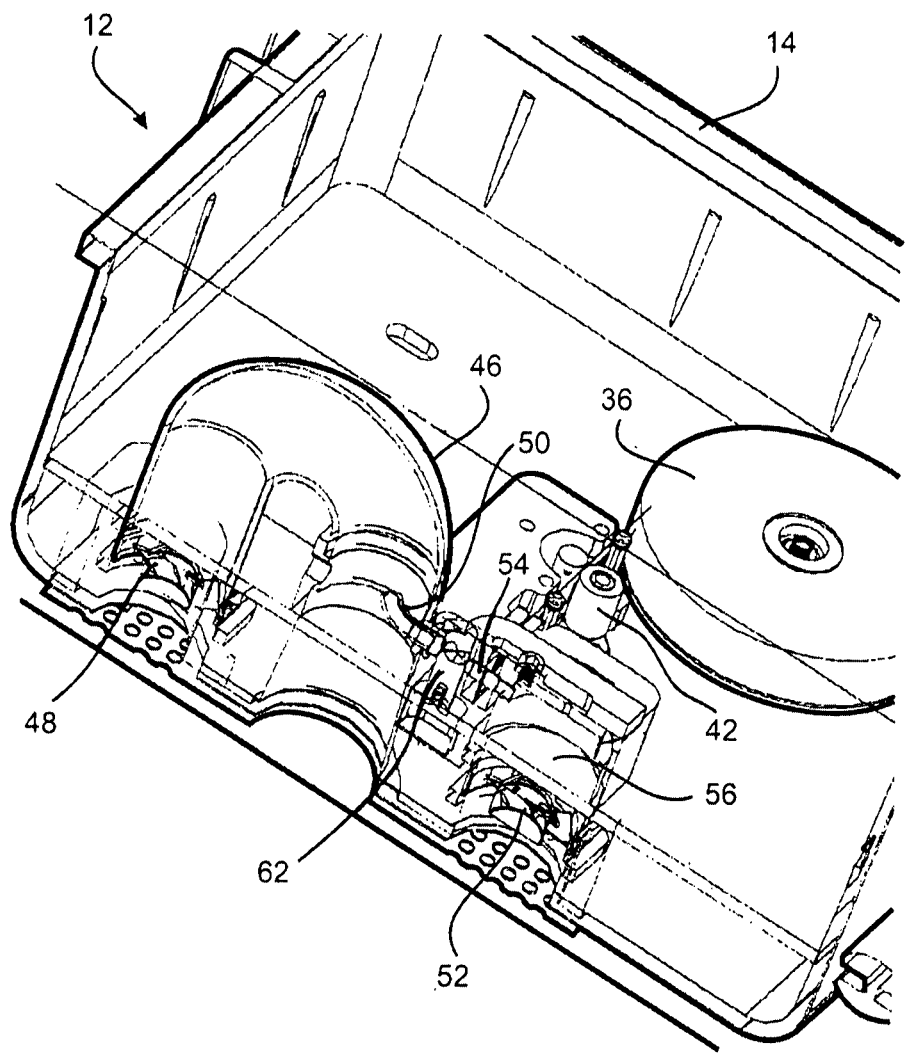
FIG. 7 shows a top perspective cut-away view through the line A-A in the dust collection module of FIG. 6.
Figure 8:
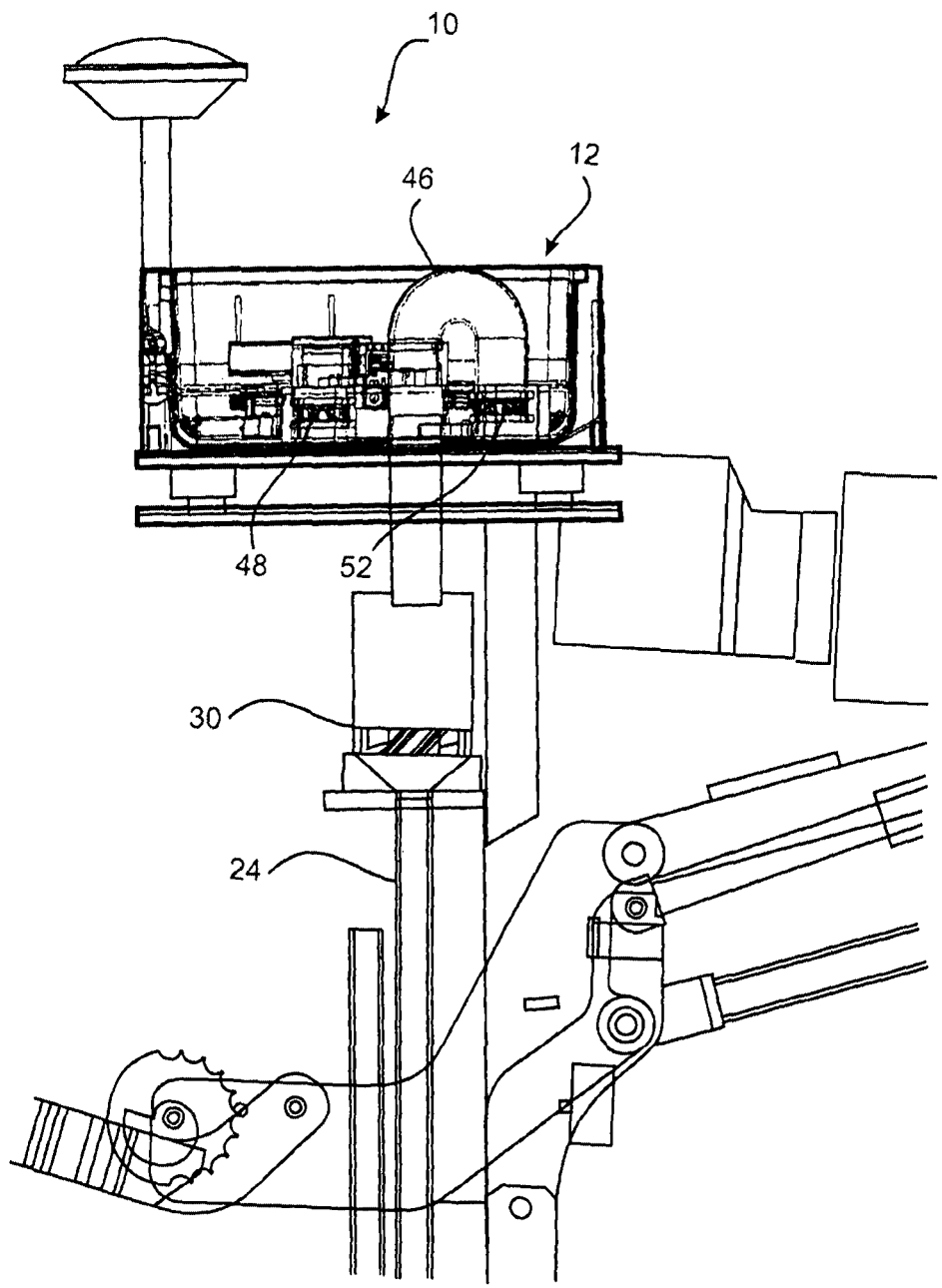
FIG. 8 shows an enlarged side elevation cut-away view through the system for collecting dust samples of FIGS. 1 to 3.

The dust collection module 12 preferably includes a GPS receiver for obtaining the GPS coordinates of the location of each dust sample collected by the system 10. A microprocessor-based controller 60 controls the operation of the various components of the dust collection module 12. The microprocessor-based controller 60 records the barcode from the filter tape 40, together with the GPS coordinates for each dust sample collected before the tape transport mechanism is activated to incrementally move the tape 40 ready for the next sample. FIG. 4 illustrates graphically a typical sequence of steps involved when collecting each dust sample.

With the sampling probe 20 in its raised position as shown in FIG. 1, the vehicle on which the system is transported may typically travel over the ground at 15 km/hr. Between dust samples, the system is purged of all dust particles to avoid contaminating subsequent samples. This is done by turning on both the mass fans 30 and 48. As the system 10 draws close to the location of the next sampling waypoint, the transport vehicle will typically slow down to 10 km/hr as the sampling probe 20 begins to be lowered to its operating position and penetrates the soil as shown in FIG. 2. When the tip of the tine on the sampling probe 20 reaches its full depth of about 100 mm, the vehicle slows to about 5 km/hr and the system 10 is ready for collecting a sample. The tine can be biased to engage into the surface of the ground a required amount. Depth maintenance can be used to ensure required depth of sampling consistently for quality control and collection purposes. Depth maintenance can be provided by a biasing means which positively encourages the tine to engage downwards into the soil, and a control means, such as a trialing wheel (e.g. wheel 29) can be used to maintain that required depth. Other depth maintenance means may be employed, such as a depth gauge and tine lifting/lowering control means, which may be motor controlled.

All the vacuum fans are turned on and a dust sample is drawn up into the dust collection module 12. Some of the fine dust particles from the main dust stream are deposited onto the filter tape 40 beside a unique barcode.

Simultaneously the GPS coordinates of the location of the dust sample are obtained and recorded together with the unique barcode for that sample read from the filter tape 40. All the fans are turned off and the sampling probe 20 is lifted back to its raised position. The dust cleaning sequence is initiated using a blast of compressed air. The filter tape 40 is then stepped through by the tape transport mechanism 32 to the next barcode sample area ready for next dust sample collection. Then the operating sequence is repeated for the next dust sample.

The operator is typically guided by a digital positioning screen that tracks his 30 path and records sample locations, while showing his position relative to a pre-planned path and distance on the screen. The digital positioning screen also includes a guidance light bar which provides a visual cue for the operator to maintain the heading of the vehicle in the correct direction. The light bar includes two zones coloured orange and red either side of a green circle in the centre of the bar, which represents the true heading. If the vehicle is heading in the correct direction the green circle in the centre lights up. If the direction of the vehicle starts to deviate to one side of the true heading the orange bar on that side lights up indicating caution. If the direction of the vehicle is not corrected the red bar on the same side lights up, warning the operator that on the current heading the vehicle will miss the next waypoint. One sample reel can typically hold up to 2000 samples, which is the expected sample collection rate per day. One cassette should therefore contain one day's worth of samples, which avoids multiple cassette changes in a days work. When the cassette is full a field collection SO memory card (see FIG. 11) is removed from the computer and placed with the cassette in a sealed cassette pod and delivered to a laboratory for analysis.

The system 10 for collecting dust samples enables automatic continuous or periodic sample collection at required speeds , such as between 2 km/hr to 50 km/hr. The speed can vary depending on the terrain (gradients, obstacles, type of soil, soil wetness etc).

The location of each sample is automatically determined with reference to a state-of-the-art GPS system. The sample collection system 10 can be programmed to collect samples according to a pre-determined grid pattern of waypoints, or simply by taking samples over the sampling area at points that can be recorded as when collection occurs. In this way it is possible relocate sample waypoints if initially unrecognised obstacles are encountered during sampling, and to increase the sampling density if in the field a particular area is considered worthy of a more detailed sampling regime.

In the option where the transporting means is a UAV, a suitable UAV would be a (computer or line of sight) controlled or autonomous UAV, such as a ducted fan craft or a miniature helicopter. The UAV can carry a lightweight dust collection module and employs fully automated preprogrammed sample waypoint coordinates in its camera-operated obstacle avoidance navigation system. It collects dust samples utilising a miniature compressed air driven probe (such as a 'dart') and dust collection head, or a weighted head that penetrates the soil to a required depth. The head or probe might be deployed from the UAV on a line, such as a wire, or on an extendable tube or rod. It is envisaged that soil sampling from a distance off up to 1.0 meter above the soil surface will be carried out. Any perceived problem of downdraft from the UAV displacing light soil from the soil surface is negated by the probe sampling below the surface. The UAV may be configured to travel and sample over land or over water. For example, over water the UAV may lower a sampling probe down through the body of water and take a sample from below the underlying bed. Over water the sampling may be carried out by the flying above contact with the water or by a vessel floating in contact with the water. Alternatively, sampling may be carried out from a manned vessel or craft on or over the water. The dust collection module 16 can be similar to the 4WD vehicle-mounted design but reduced in size and weight to reduce payload for the UAV. The power source is a NiCad or lithium ion type battery system that feeds the power to the UAV. The UAV can be operated by a single person sitting in the airconditioned comfort of a control vehicle or remote building. The dust-proof case and reels are removed from the UAV and transported by air to the laboratory for subsequent analysis, same as the conventional 4WD design. The UAV allows locations that are otherwise difficult to access to be reached, for example, pockets of wooded terrain. The UAV might be fitted with visual means, such as monocular or binocular camera system, which can either record sampling operations or feed video data back to an operator for "real time" viewing and control purposes.

The 4WD-mounted system 10 for collecting dust samples can be incorporated onto a purpose-built fully integrated tray body that incorporates the hydraulic and pneumatic powerpack and controls. This design allows the sampling probe 20 to be mounted within the 1 meter overhang limits set by the Australian Department of Transport industry safety standards. The standard tray of a dual cab 4WD is removed and the fully integrated tray body bolted onto the 4WD chassis. This design optimises mechanical strength, whilst improving operator safety, portability to any location in the world. It also places all the equipment and cable looms in a single transportable package that can be AS checked prior to shipment.

Alternatively the system 10 for collecting dust samples can be mounted on a bogy trailer with airbag suspension. A hitch-mount adjuster can be used to maintain the correct ground engaging height of the depth-control mechanism 28 to ensure the depth of the tine 22 is maintained at 100 mm below ground at al times. The pneumatic and hydraulic power-pak and all other equipment is also mounted in the trailer unit which is of similar design to the fully integrated tray body for the 4WD described above. The trailer unit can be towed by any suitable vehicle, and thus is not restricted to 4WD terrain—an all-terrain vehicle can be employed that has the ability to tow and operate in hostile conditions and difficult terrain. The trailer unit also permits a 0.03 micron air filtration system to be incorporated, using a chiller operated by a 240 volt or 12 volt diesel powered generator mounted on the trailer. This filtered and dehumidified air is used to clean any residual dust remaining in the dust collection pathway to prevent contamination of the dust samples.

A preferred embodiment of a system and method of collecting and analysing dust samples from a geographical area for locating subsurface ore bodies will now be described with reference to FIGS. 9a to 12.

Figure 9A:
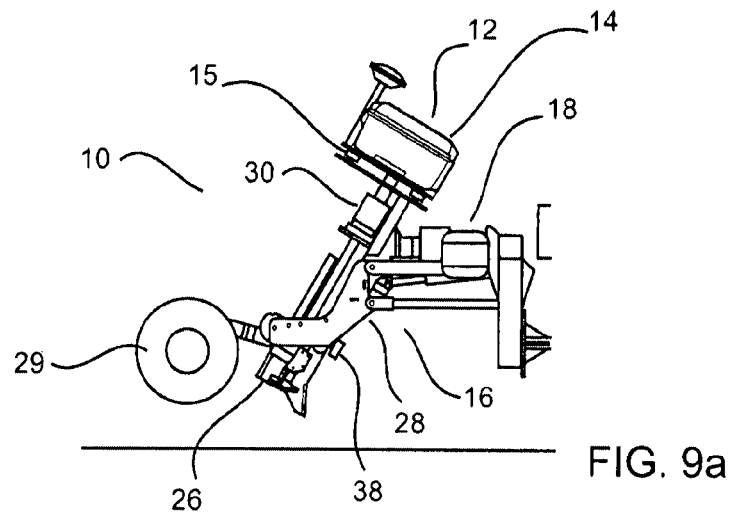
FIGS. 9a-9o are schematic drawings showing stepwise employment of a system for collecting dust samples for use in analysis, in accordance with a preferred embodiment of the present invention.
Figure 9B:
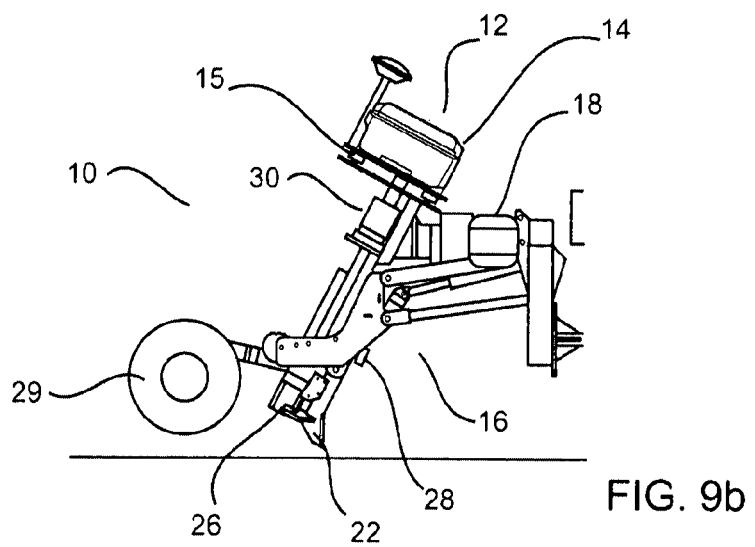
FIGS. 9p-9u are schematic drawings showing steps in retraction of the tine from the ground, and purging of the tube prior to collection of a subsequent sample according to an embodiment of the present invention.
Figure 9C:
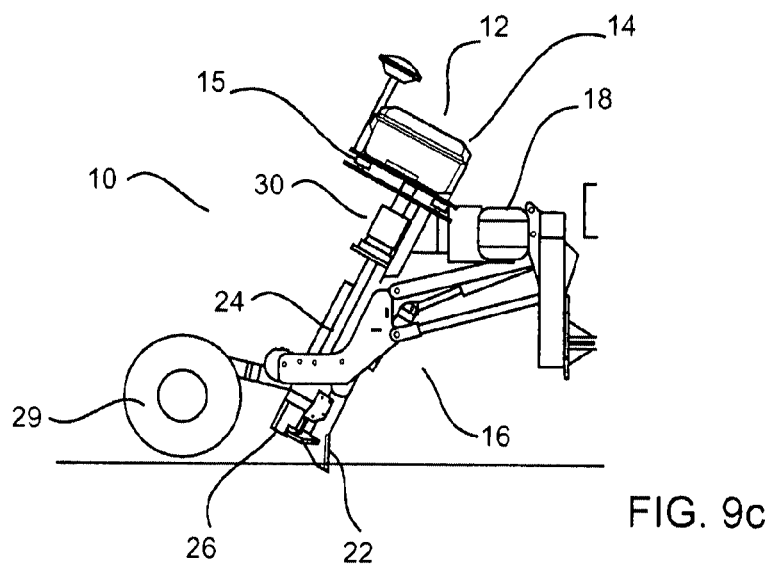
Figure 9D:
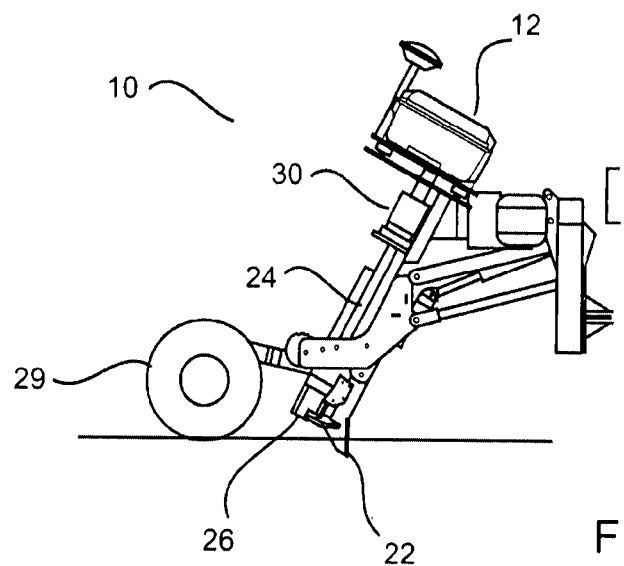
Figure 9E:
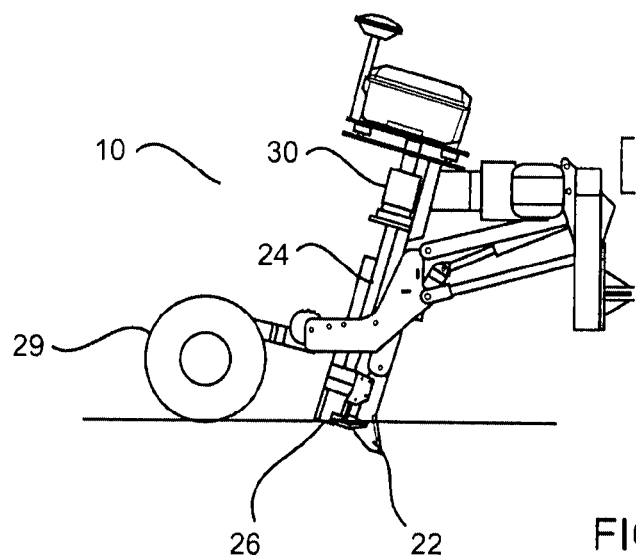
Figure 9F:
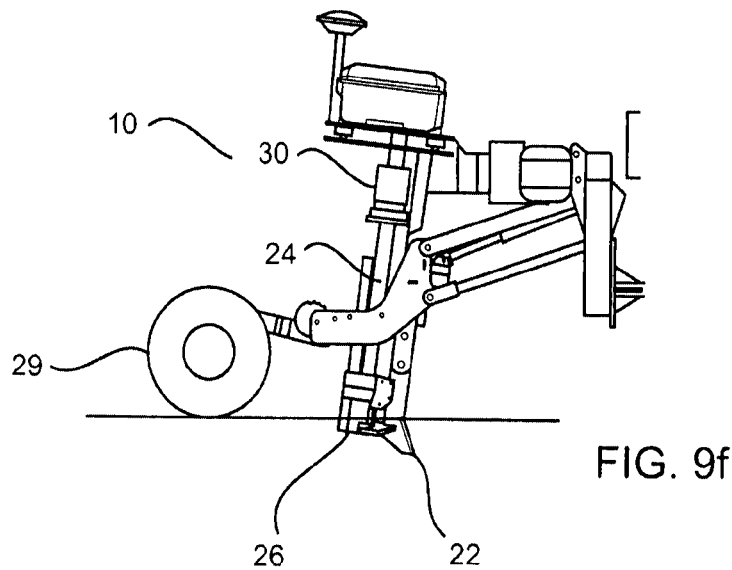
Figure 9G:
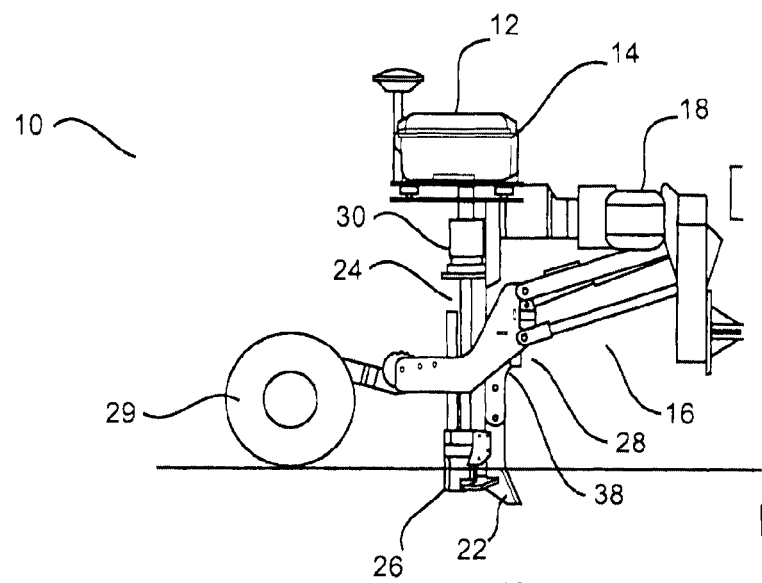
Figure 9H:
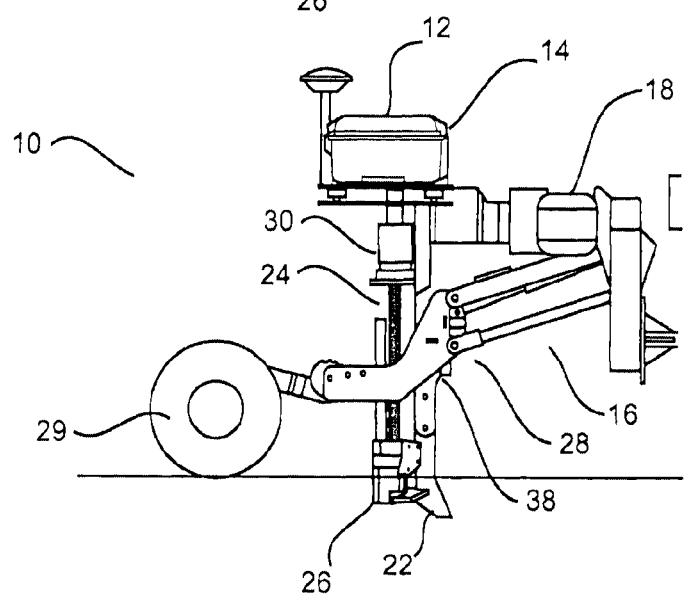
Figure 9I:
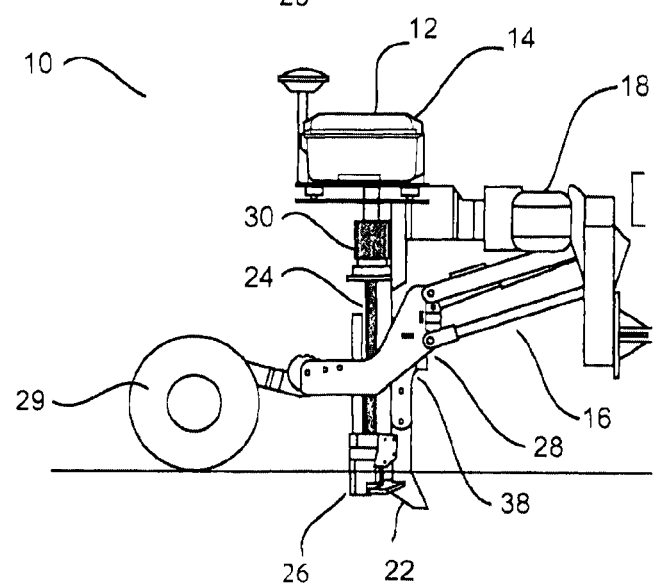
Figure 9J:
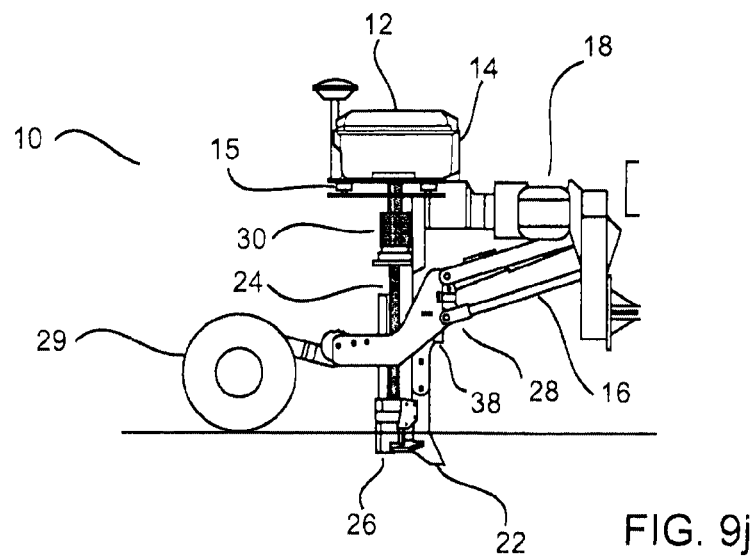
Figure 9K:
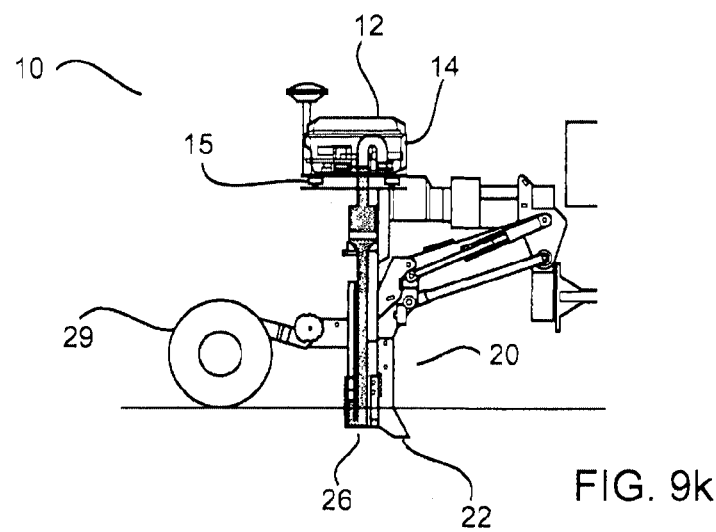
Figure 9L:
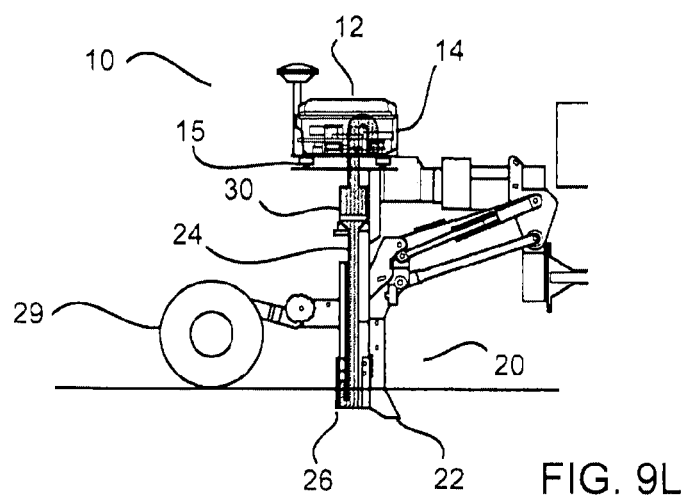
Figure 9M:
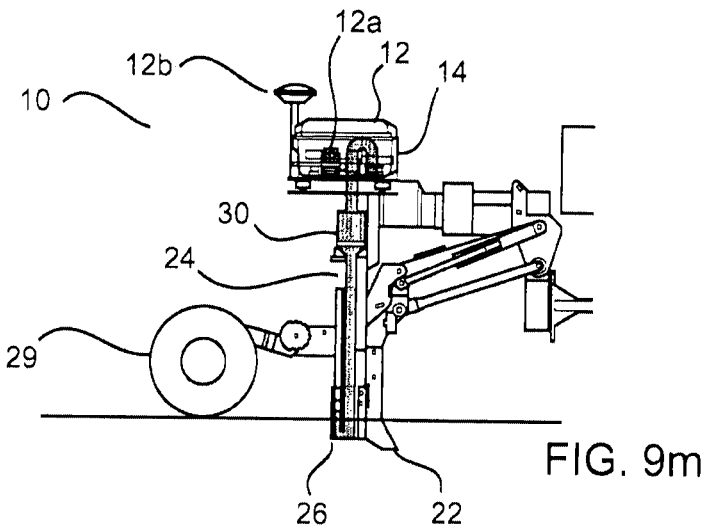
Figure 9N:
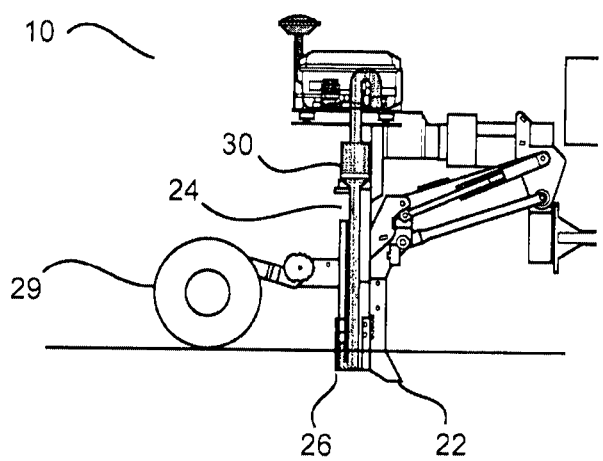
Figure 9O:
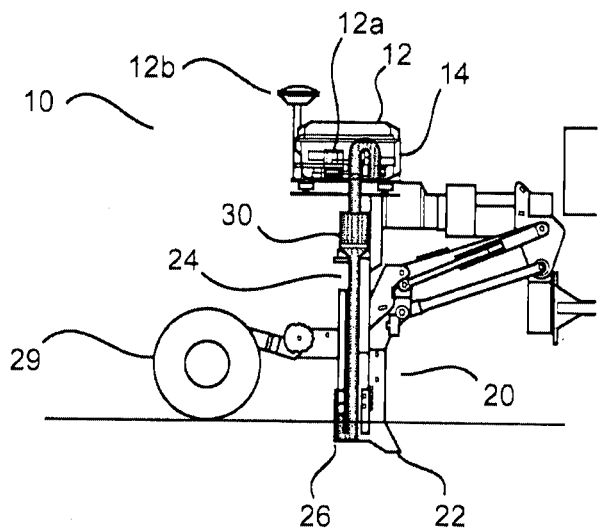
Figure 9P:
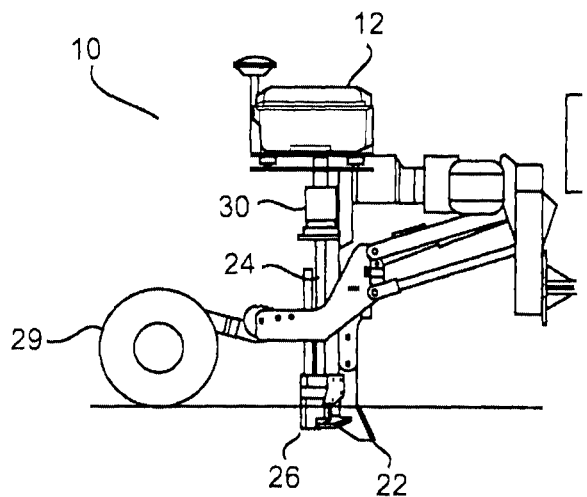
Figure 9Q:
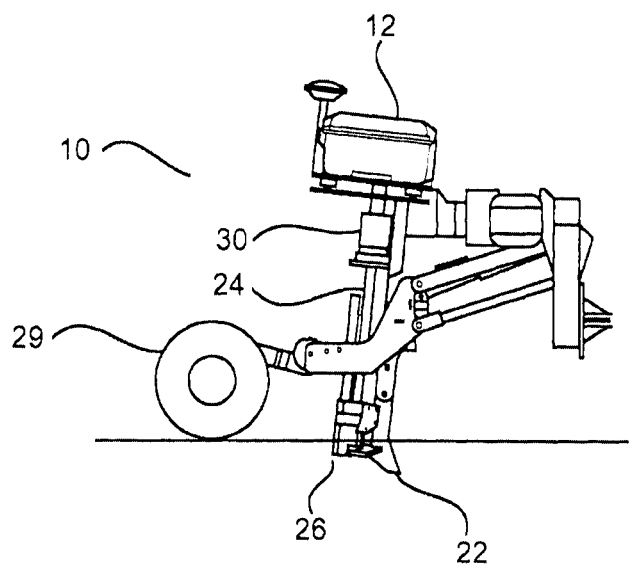
Figure 9R:
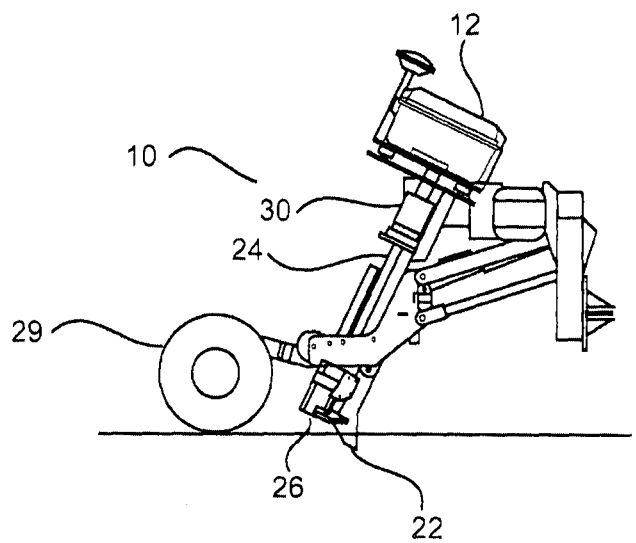

FIGS. 9a-9o show stepwise employment of a system for collecting dust samples for use in analysis. The system 10 is mounted to the rear of a vehicle as shown in FIG. 1, and the same reference numerals are used.

As the vehicle moves forward (i.e. to the right as shown in the figures), the tine 22 is gradually lowered and engages into the soil surface. At FIG. 9g the tine 22 is in its lowermost position and the sample (dust) collection tube 24 is upright with the sample collection tube opening at approximately 100 mm from the soil surface.

As shown in FIG. 9h, the mass fan is running and a soil sample is traveling up the sample collection tube 24 from the opening at the bottom of the collection tube. In FIG. 9i, the sample is passing through a cyclonic separator 30 to remove larger particles of soil.

In FIGS. 9j to 9o, the sampling fan is running in the dust collection module 12. This fan extracts dust from the sample above the cyclonic separator.

In FIG. 9m, a vacuum fan 12A is run to extract fine dust particles from the sample via a capture medium, such as a tape. The fine dust particles are essentially blown onto and captured by the medium. Each fine dust particle sample is indexed with a unique reference identifier. In FIG. 9n, GPS positioning equipment 12B is used to obtain coordinates for the soil sample collection location.

FIG. 9o shows the system 10 with vacuum turned off—sample collection and transfer of fine dust particles to the capture medium (eg tape) is completed for that sample.

Figure 9S:
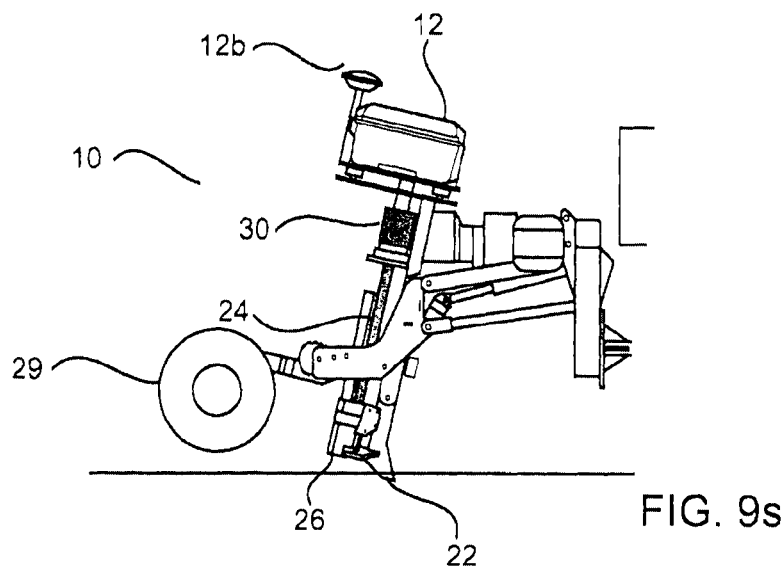
Figure 9T:
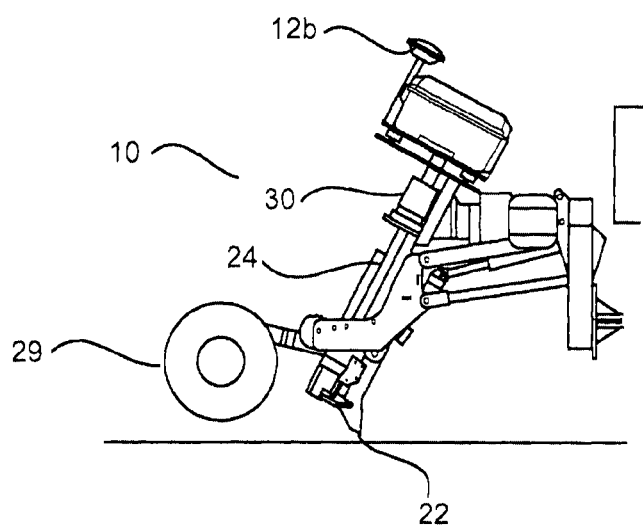
Figure 9U:
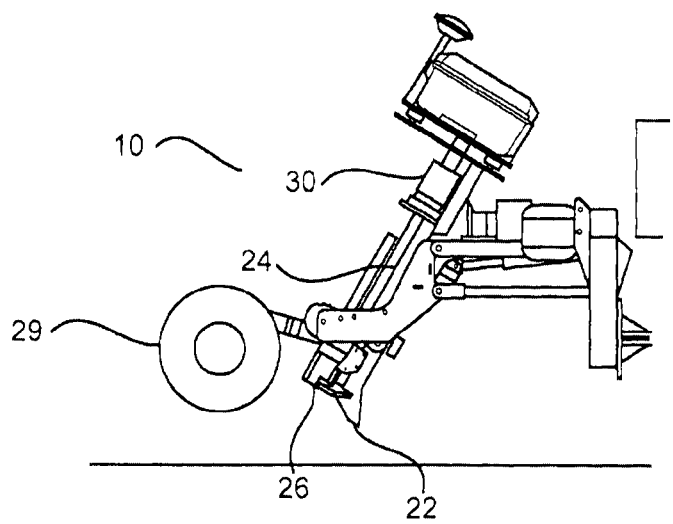

FIGS. 9p to 9u show various stages of lifting the tine 22 after sample capture. FIG. 9s shows the mass fan cleaning out the collection tube by blowing particles back through the cyclonic separator and down the tube to be exhausted at the tube inlet/outlet. This process 'cleans' the collection tube and separator ready for the next sample and avoids contamination of that next sample by dust from a previous sample.

Dehumidified and pre-filtered gas (preferably air, though nitrogen may be used) at pressure may be employed to clean the collection tube (and preferably other zones) of contaminant. The air is pre-filtered of any contaminant and dehumidified to prevent moisture and material depositing in the moist zones which could build up and cause a block or contamination.

The system 70 for analysing dust samples, as shown in FIGS. 10a to 10d, typically comprises an ablation means 76 for ablating particles of dust from the dust sample collected in the field and analysis means for analysing the chemical composition of the ablated dust particles for the presence of hydromorphic anomalies that may indicate the mineralogy of subsurface ore bodies.

Figure 10A:
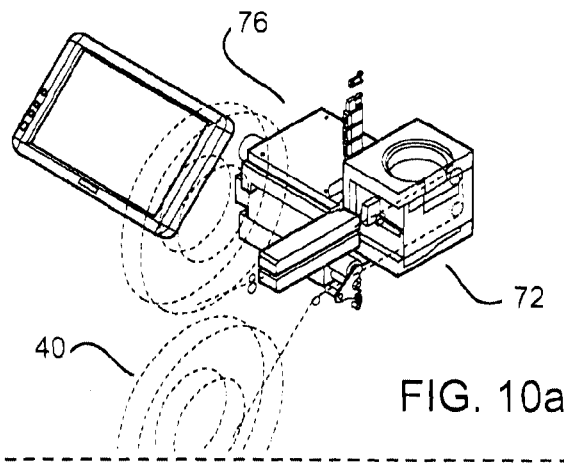
FIGS. 10a-10d show loading of a medium bearing collected samples into part of a system of a preferred embodiment of the present invention, the system including a laser ablation device and a mass spectrometer, and diagrammatic steps in purging the laser ablation device and carrying out spectroscopy on the collected samples.
Figure 10B:
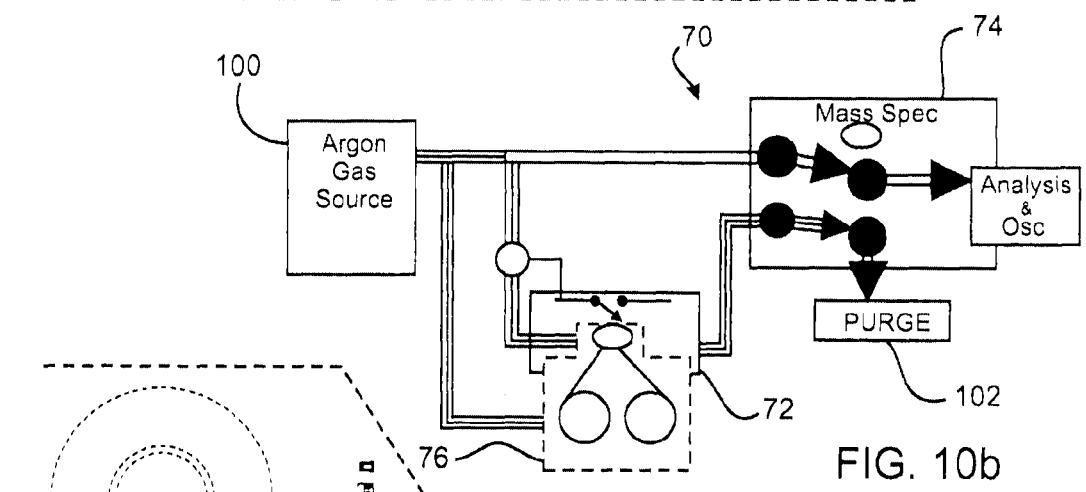

In the illustrated embodiment shown in FIG. 10b, a laser ablation cell 72 is provided for extracting dust particles deposited on the filter tape 40 and ablating the particles in an atmosphere of inert gas 100 (argon). The ablated material is then conveyed to a mass spectrometer 74 for analysis of the chemical components, including any hydromorphic anomalies that may be present in the sample. The laser ablation cell and the mass spectrometer are first purged via a purge means 102 with argon gas prior to analyzing a sample. This removes any contamination that may linger from a previous sample or from ambient air. One bar pressure of argon may be used. Loss of argon gas and contamination during auto ablation of the samples is prevented by utilising a pressure vessel that contains the argon and the tape holding the samples for ablation. A gas lock valve arrangement within the ablation unit can be used to maintain a contamination free zone immediately surrounding the ablation zone within the ablation unit. This gas lock valve arrangement involves at least one valve between the supply of argon and the ablation unit, whereby the gas supply and the ablation unit become isolated from one another during ablation. This prevents matter during ablation from entering back towards the gas supply and subsequently contaminating the next sample ablation.

A valve can be used to seal argon at a sample to be ablated. The valve can be air operated or electrically operated. The sample on the tape is subjected to approximately 1 bar argon pressure, such that any oxygen or air is purged away from the sample to be ablated. Once ablation of that sample is complete, the valve can be opened to allow for the next sample.

Figure 10C:
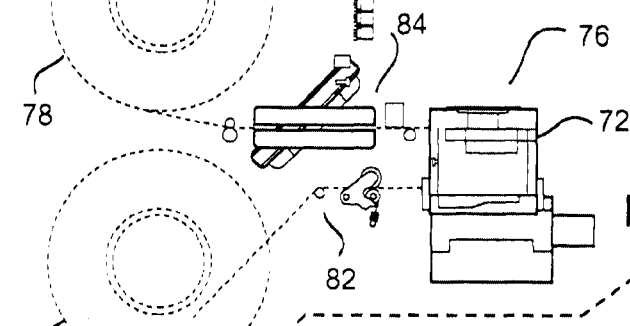

FIG. 10c illustrates in more detail the arrangement of the auto ablation assembly 76 for the system 70 of FIG. 10a. The auto ablation assembly 76 comprises means for receiving a sample reel 78 with the coded filter tape 40 having particles of dust deposited thereon from each dust sample collected. It includes a tape transport mechanism 80 for receiving the sample reel 78 and transporting the filter tape 40 in a contamination-free environment to a take-up reel 82. The laser ablation cell 72 is provided in connection with the tape transport mechanism 80 for ablating particles of dust from each dust sample as the tape passes through the cell. A barcode reader 84 is provided for reading the unique identifying code for each dust sample from the filter tape 40 as the tape is stepped through the ablation cell 72.

Figure 10D:
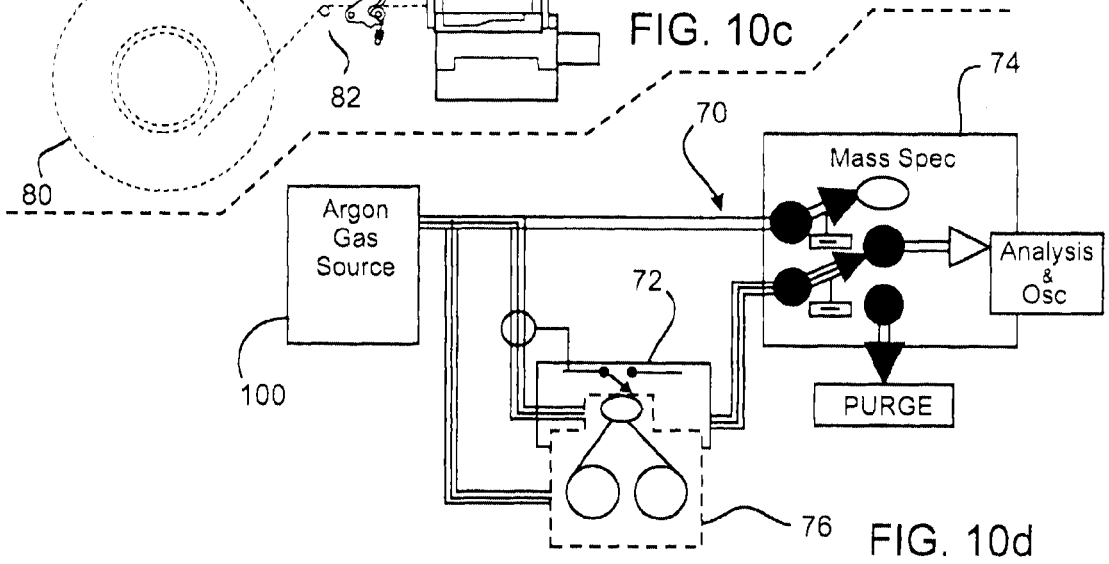

FIG. 10d shows the arrangement of FIG. 10b with the ablated sample being analysed by the mass spectrometer to detect presence of hydromorphic anomalies. Analysis is carried out in the inert gas environment, such as in argon, preferably at up to one bar gas pressure.

Ablation may be continuous or stepwise, as may be sample collection. For example, instead of periodic sampling the system may continuously sample and obtain a continuum of samples and analyse such samples to obtain an indication of continuity of presence of anomalies.

Figure 11:
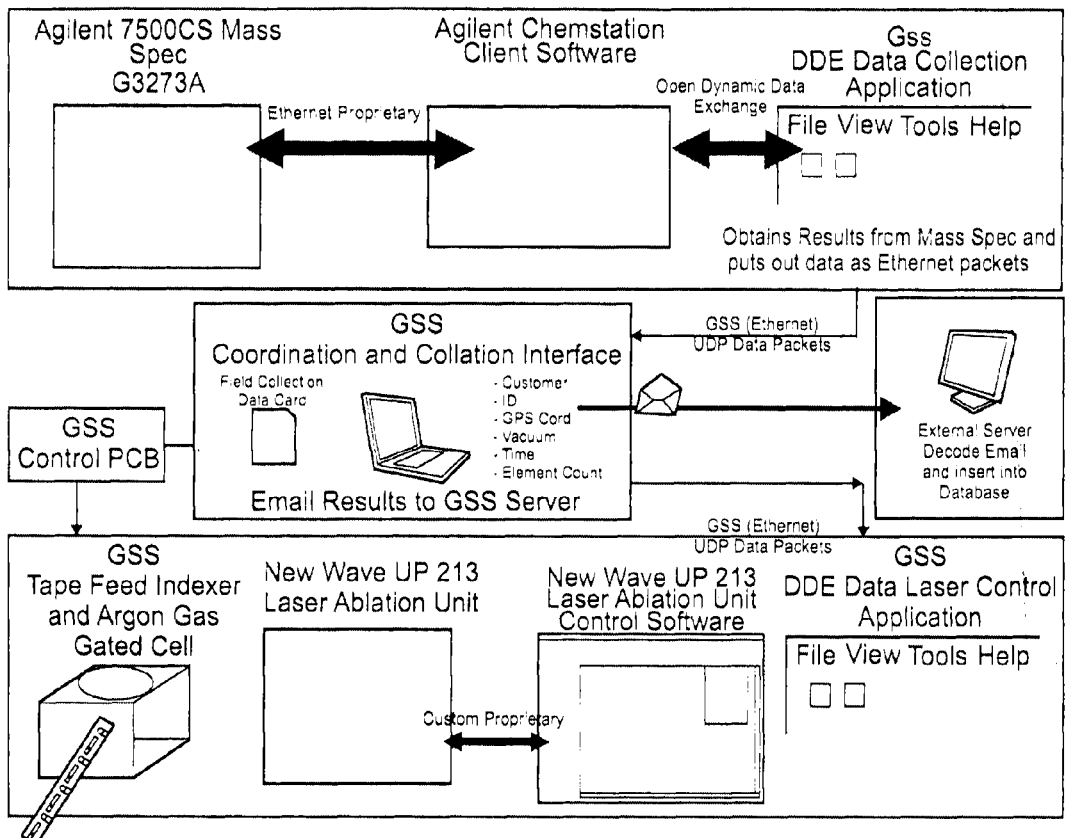
FIG. 11 illustrates a method of processing dust samples in accordance with an embodiment of the present invention; and, FIG. 12 illustrates a typical map generated in accordance with a preferred method of the present invention, giving a graphical representation of the potential mineralisation of subsurface ore bodies derived from analyzing the collected samples.

FIG. 11 illustrates a typical sequence of steps involved in the method of processing the collected dust samples in a laboratory. The cassette containing the coded filter tape 40 with the particles of dust deposited thereon is placed 100 in the auto ablation assembly 76. The filter tape 40 is then transported in a contamination-free environment through the laser ablation device 72, and dust from each dust sample are ablated. The unique identifying code for each dust sample is also read from the filter tape. After ablation the tape transport mechanism 80 moves the tape 40 along, and accurately positions the tape ready for the next laser ablation process. Analysis 102 of the ablated materials is performed in the mass spectrometer 74 to obtain concentrations that can be used for detecting chemical anomalies.

Figure 12:
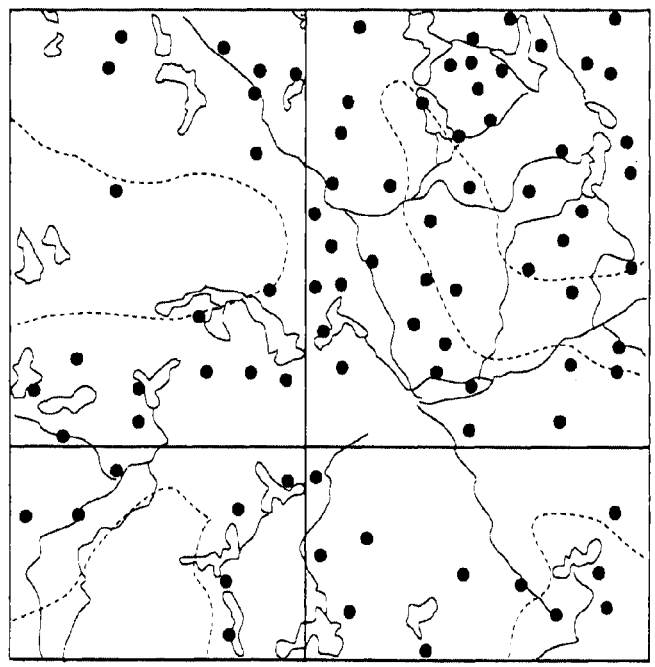

A system computer programme 80 digitally records 104 the results of the geochemical analysis, the unique identifying barcode, and the GPS coordinates of the location for each dust sample from which the dust particles have been obtained whereby, in use, the recorded data can be used to identify the potential mineralisation of subsurface ore bodies. The recorded data can be used for generating a visual representation of possible subsurface mineralization in the geographical area from which the dust samples were collected. A sample map is illustrated in FIG. 12 showing the results of the geochemical analysis and the location of sampling waypoints.

Once the results of the geochemical analysis of the fine particles of dust are known, the indications of mineralisation suggested by any superimposed hydromorphic anomalies in the dust particles are averaged 106 and combined with the GPS coordinates of the dust particles. The results of the averaging are then superimposed 108 on a map of the geographical area using different colours to generate a "halo effect", as shown in FIG. 12, indicating the possible mineralisation of subsurface ore bodies. Live data from the laser ablation analysis can be automatically downloaded to a digital mapping system that shows up to 80 elements as a halo effect around mineralisation "hotspots."

Thus the location of subsurface ore bodies can be quickly identified whilst the geologist is still on site. Additional samples can then be collected in potential hotspots to verify and provide a more complete picture of the potential mineralisation of subsurface ore bodies.

As illustrated in FIG. 11, proprietary client software is employed to access the mass spectrometer client application and to transfer the results of the chemical analysis to a Coordination and Collation Interface using the 19 Dynamic Data Exchange (DOE) protocol. The data is transmitted to the Coordination and Collation Interface via an Ethernet as UDP data packets. The data from the field collection memory device (an SD card in this embodiment) is also provided to the Coordination and Collation Interface and the results are emailed to the server. The server decodes the email and stores the data in a database.

Sample waypoint coordinates can be preloaded prior to arriving at a site to be surveyed, or immediately prior to commencing surveying, or can be loaded consecutively as the sampling is progressing provided at least the next required coordinates are loaded prior to being needed. The field collection unit uses a digital navigation system to track the sample collection zone and collect each sample.

A Control PCB is designed to control operation of the auto ablation assembly 76. A DOE laser control software application is employed to control the laser ablation cell 72.

Hence the system is capable of automatically advancing each sample on the filter tape 40, controlling the ablation device 72 and controlling the flow of gas, including purging when necessary. It reads the barcode, initialises the mass spectrometer and the laser ablation unit. Then it ablates the sample, obtains the results from the mass spectrometer and records the results into the proprietary GSS database. Typical database records for each sample 15 include Customer 10, Sample 10, Collection Unit Serial Number, GPS coordinates, Time and Date of sample, Sample Vacuum, Sample Collection Time Interval and Ablation Results. The system 70 for analysing the dust samples can be built as a transportable unit and taken into the field to improve sample analysis and turnaround time.

One or more digital images of the topography to be surveyed can be captured before, during or after sampling, preferably before sampling. Each image can be associated to one or more samples collected and analysed. For example, images of 40 sq meter areas can be imaged, whereby each image relates to an individual sample. Each image can therefore be indexed to the respective identifier for each respective sample e.g. an image can be matched to a barcode associated with a particular sample on the tape. The images can be used by a Geologist to assist greatly in the interpretation of the digital data sets of the corresponding sample.

Now that a preferred embodiment of the system and method for locating subsurface ore bodies has been described in detail, it will be apparent that the described embodiment provides a number of advantages over the prior art, including the following:

i) The methodology is based on analysis of dust particles as they occur in nature and therefore there is no sample preparation of collected material required prior to analysis.

ii) The potential for contamination of preparative reagents is therefore eliminated.

iii) Since only a small portion of each dust sample is destroyed during the analytic process, a significant amount of the collected sample remains for future or repeat analysis.

iv) Dust samples can be collected rapidly and in large quantities over a sizable geographical area in a single day, significantly improving the efficiency and reducing the costs of sample collection.

v) Small size dust particles means that the ratio of hydromorphically deposited ions to the particle mass when both are ablated is much greater than for larger dust and soil grains. The focus on fine dust particles (preferably less than 4.0 micron size) allows greater differentiation from background levels of ions/elements vi) The dust collection module is relatively lightweight (typically no more than 5 kg) and therefore can be easily transported on a variety of vehicle platforms or carried by foot.

vii) Laboratory analysis of dust samples can also be fully automated to increase the speed at which the samples are processed and analytic data is available for mapping.

Collect samples on tape

Seal and transfer tape to analytical laboratory

Introduce tape into newly designed tape holder in LA-ICP-MS instrument

Calibrate system using Certified Reference Materials (CRM's)

Set up software so that the instrument will analyze the tape samples and relate each sample to its geographical location Run all samples on tape Remove all data from instrument electronically and either run through expert system (yet to be designed or manually look at data to determine if there are any anomalous readings that are the result of photon incidents during the analytical run Take final data set and plot data in terms of northing's and easting's for individual elements relevant to t he particular type of investigation being undertaken (there are different element profiles indicating subcropping mineralization for different exploration initiatives.

Plot combined elemental profiles in the same manner (there are different multi-element suites representing different types of mineralization)

Overlay relevant plots on known subcropping geology (manually or with program when developed)

Identify areas of potential subcropping mineralization (manually or with program when developed)

Draw relevant exploration maps identifying areas of potential subcropping mineralization on the map.

Figure 13:
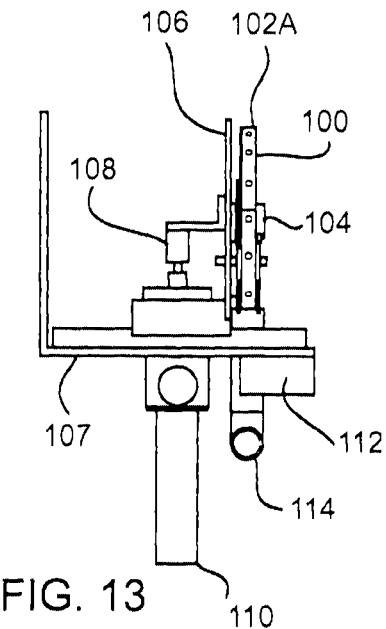
FIGS. 13 and 14 show an alternative arrangement of the filter medium on spools or reels of an embodiment of the present invention using a shuttle mechanism.
Figure 14:
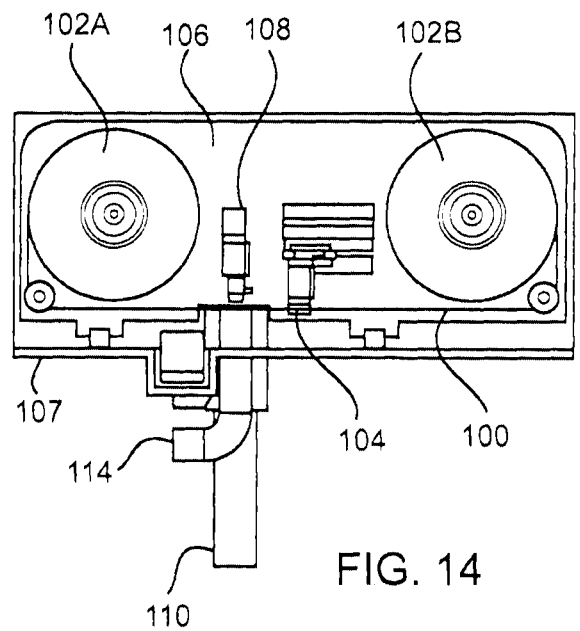
Figure 15:
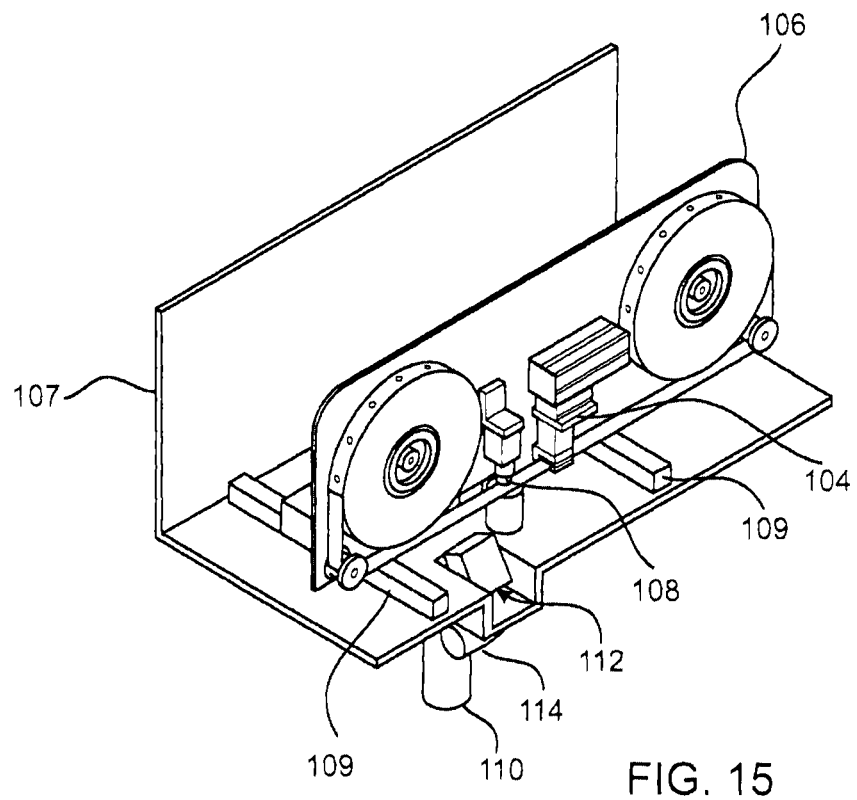
FIGS. 15 and 16 show the shuttle mechanism of FIGS. 13 and 14 in two positions.
Figure 16:
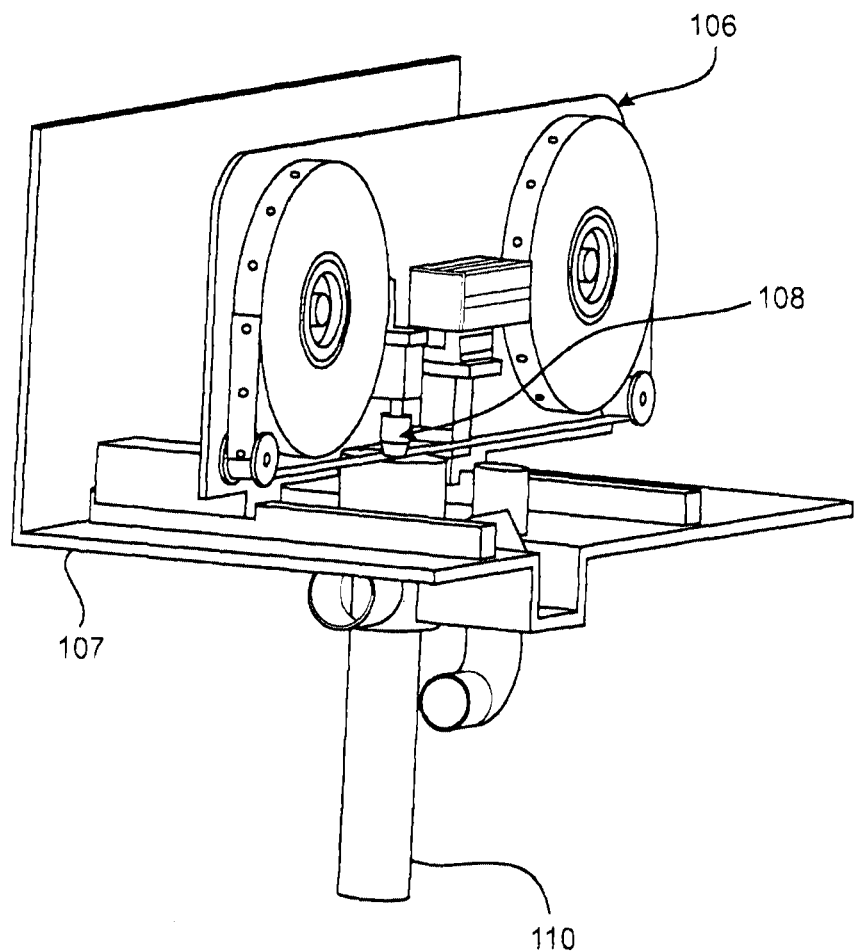

FIGS. 13 and 14 show an alternative embodiment of the filter medium arrangement. The filter medium 100 is a tape on two reels/spools 102A, 102B. The tape is advanced and indexed by a tape indexer 104. The tape indexer 104 grasps or holds the tape and advances it a required distance from one reel/spool onto the other reel/spool. There are two positions for the mechanism holding the reels/spools. The first is a cleaning position and the second is a sampling position. The mechanism moves on shuttle guides, such as rails 109. Thus, this mechanism shuttles the reels/spools from one position to the other and back. A drive means, such as a motor or air drive can be employed to effect movement. Tape is spooled from reel/spool 102A to 102B while at its cleaning position and the barcode is read. The tape is advanced one sample position. While this is happening, the sampling tube and dust chamber are cleaned (position at FIG. 15). When tape indexing and cleaning are complete, the shuttle assembly 106 (mounted on a mounting plate 107) is moved relative to the mounting plate to the sampling position (position at FIG. 16). At the sampling position, the sample vacuum 108 advances and dust is sucked up the sampling tube 110. When dust flow is established, the vacuum is turned on and dust is sucked onto the sample filter medium (tape 100). When complete, the sample vacuum retracts, the shuttle is returned to the cleaning position and the cycle is repeated for the next sample. A laser barcode scanner identifies the indexed mark on the tape relating to a particular sample. Excess dust is extracted via an excess dust extraction tube 114.

It will be readily apparent to persons skilled in the relevant arts that various modifications and improvements may be made to the foregoing embodiments, in addition to those already described, without departing from the basic inventive concepts of the present invention. For example, in the described embodiment ablation is carried out in argon in order to permit the dust particles deposited on the filter tape to be ablated in an inert atmosphere. However, the same result may be achieved by placing the entire auto ablation assembly, including the tape transport mechanism, in a sealed enclosure, evacuating the enclosure and filling it with an inert gas. Therefore, it will be appreciated that the scope of the invention is not limited to the specific embodiments described.

The invention claimed is:

1. A method for locating subsurface ore bodies, the method comprising: transporting a dust collection apparatus over an aboveground surface of terrain of a geographical area, taking samples of sub-surface soil containing dust particles into the dust collection apparatus at a depth of up to 1 meter below the aboveground surface of the terrain at locations within the geographical area by inserting a dust sample collection tube into the aboveground surface of the terrain to the depth of up to 1 meter and sucking the sub-surface soil containing the dust particles into the dust collection apparatus using the dust sample collection tube at the locations within the geographical area, capturing dust particles from respective dust samples onto a tape, and associating the captured dust particles of each dust sample at a respective sample position on the tape with a unique identifier, the captured dust particles on the tape being for analysis to discover any chemical anomalies in the dust particles as a way of identifying possible subcropping mineralization.

2. A method according to claim 1, further comprising: establishing waypoints for taking the dust samples in a preselected geographical area; and taking a sample of the sub-surface soil containing the dust particles at each waypoint and simultaneously recording the GPS coordinates of each waypoint.

3. A method as claimed in claim 1, further comprising storing the dust samples in a contamination-free environment for conducting the analysis of the dust samples for hydromorphic anomalies in the dust samples.

4. A method as claimed in claim 1, further comprising:
the transporting of the dust collection apparatus over the terrain in the geographical area being according to predetermined waypoints;
inserting the dust sample collection tube into the sub-surface soil at selected ones of said waypoints;
storing the dust sample from each waypoint in the dust collection apparatus in a contamination-free environment; and,
recording the GPS coordinates of each selected waypoint whereby, in use, analysis of the dust samples for any hydromorphic components in the dust samples is used to determine the potential mineralisation of subsurface ore bodies.

5. A method as claimed in claim 1, further comprising: generating a visual representation of the distribution of possible sub-surface mineralization in the geographical area based on results from the analysis.

6. A method according to claim 4, wherein
recording the GPS coordinates of the location of each dust sample is conducted substantially simultaneously with the collecting and storing of the dust samples.

7. A method according to claim 1, further comprising averaging the results of the analysis.

8. A method as claimed in claim 7, further comprising combining GPS coordinates of geographic locations from where the dust particles are sampled with results of statistical manipulation of data, and superimposing on a map of the geographical area the results of the statistical manipulation of data to generate a plot to indicate the potential presence of sub-surface mineralization.

9. A method as claimed in claim 1, further comprising: capturing the dust particles from each dust sample collected at a respective waypoint onto the tape and wherein the tape is an indexed tape.

10. A method as claimed in claim 1, wherein the dust samples are sucked onto or blown onto the tape.

11. A method as claimed in claim 9, wherein the dust samples are obtained from between 75 mm and 200 mm below the aboveground surface of the terrain.

12. A method as claimed in claim 1, wherein the dust particles for analysis include dust particles up to 5.0 micron in size.

13. A method as claimed in claim 1, wherein the dust particles for analysis predominantly include dust particles up to 10.0 micron in size.

14. A method as claimed in claim 1, further comprising transporting the tape having indexing for each captured dust sample from a first reel onto a second reel in a contamination-free environment.

15. A method as claimed in claim 14, wherein each unique identifier includes a unique identifying code, and the method further comprises
reading the unique identifying code for each of the indexed dust samples from the indexed tape, and
storing GPS coordinates together with the unique identifying code for each dust sample whereby, in use, subsequent analysis of dust samples is used to identify potential sub-surface mineralisation.

16. A system for collecting dust samples from a geographical area for locating subsurface ore bodies, the system comprising:
a dust collection module for storing the dust samples in a controlled environment;
transportation means for transporting the dust collection module over an aboveground surface of a terrain in the geographical area;
a sampling probe mechanically coupled to the dust collection module, the sampling probe including a dust sample collection tube;
an insertion means actuated in use to insert the dust sample collection tube into the aboveground surface of the terrain to collect the dust samples from a depth below the aboveground surface of the terrain of up to 1 meter at selected locations of the geographical area;
sampling means including a suction means provided in connection with the dust sample collection tube for drawing the dust samples up into the dust collection module by suction within the dust sample collection tube inserted into the terrain up to the depth of up to 1 meter, and
a tape onto which dust particles of each of the dust samples are captured at a respective sample position on the tape, including a unique identifier for the dust particles captured for each dust sample, for subsequent analysis to identify any hydromorphic components in the dust samples as an indication of the potential presence of sub-surface mineralization.

17. A system as claimed in claim 16, wherein the dust collection module comprises:
a container for storing dust samples in a contamination-free environment; and
a transport mechanism for the tape being an indexed tape housed within the container.

18. A system as claimed in claim 17, wherein a unique code is provided as part of the unique identifier for the captured dust particles of each said dust sample indexed on the tape; and
the system includes a code reader provided to read the unique code for the dust particles captured for each said dust sample indexed on the tape.

19. A system as claimed in claim 16, wherein the sampling probe comprises:
a tine adapted to penetrate surface overburden soil;
the dust collection tube provided in connection with the tine for transporting each dust sample from adjacent a tip of the tine to the dust collection module.

20. A system as claimed in claim 16, comprising an ablation means arranged to ablate the dust particles on the tape for analysis including the dust particles of less than 5.0 microns from a collected dust sample.

21. A system as claimed in claim 20, wherein the ablation means is housed in the dust collection module.

22. A system as claimed in claim 16, further comprising:
a sample reel holding the tape as an indexed tape for retaining the dust particles deposited thereon from each dust sample collected;
a tape transport mechanism for receiving the sample reel and transporting the tape in a contamination-free environment to a take-up reel; and
wherein the sample reel is housed in the collection module.

23. A system as claimed in claim 16, further comprising an analyzer for performing geochemical analysis of ablated dust particles for detecting hydromorphic anomalies.

24. A system as claimed in claim 23, wherein the system provides a unique identifying code as part of the unique identifier and GPS coordinates of the location for each dust sample from which the dust particles have been obtained.

25. A system as claimed in claim 16, wherein the tape includes webbing allowing relatively large particles through, and a filter medium of the tape is electrostatically charged to retain relatively smaller particles.

26. A system as claimed in claim 18, wherein the indexed tape has an electrostatic charge that retains collected said dust samples.

27. A system as claimed in claim 16, including a valve arrangement to isolate at least one of said dust samples in an argon rich atmosphere during ablation.

28. A system as claimed in claim 27, the at least one valve including an air or electrically operated valve.

29. A system as claimed in claim 16, further including image capture means arranged and configured to capture at least one image of an area of topography to be sampled, wherein each collected dust sample is identified with a particular image to locate that respective sample to the particular area of topography.

30. A method according to claim 9, wherein the dust particles of each of the dust samples captured onto the tape are moved away from and sealed from the dust collection tube after capture of the dust particles onto the tape, and the dust collection tube undergoes cleaning with pressurised, dehumidified, pre-filtered compressed air.

31. A method according to claim 30, wherein a control system moves the tape to a next sample ready position during the cleaning.

32. A method according to claim 13, whereby sub 5.0 micron dust particles form a greatest proportion of the dust particles for analysis.

33. A system as claimed in claim 16, wherein the system captures a greater proportion of sub 5.0 micron particles for analysis than any larger collected particle.

34. A method according to claim 1, including removing contaminating dust particles from a previously taken sample by purging the dust sample collection tube between taking samples of the dust particles.

35. A method according to claim 34, including purging the dust sample collection tube by blowing air through the dust sample collection tube.

36. A system according to claim 16, including a purging means to purge the dust sample collection tube of contaminants from previous sampling prior to taking a next sample.

37. A system according to claim 36, wherein the purging means includes at least one fan for blowing filtered air through the dust sample collection tube.

38. A system according to claim 16, including a control system and tape indexing system to move the tape to a next dust sample capture ready position.

39. A system according to claim 38, including a tape sealing means which seals the captured dust particles of the dust sample from the dust sample collection tube after capture of the dust particles of the dust sample onto the tape.

* * * * *